US011529154B2

(12) United States Patent
Ciccone et al.

(10) Patent No.: US 11,529,154 B2
(45) Date of Patent: Dec. 20, 2022

(54) STOOL MANAGEMENT SYSTEM

(71) Applicant: WilMarc Holdings, LLC, Fort Collins, CO (US)

(72) Inventors: Paul C. Ciccone, Wellington, CO (US); Kathryne Rose Eckert, Fort Collins, CO (US)

(73) Assignee: Wilmarc Holdings, LLC, Fort Collins, CO (US)

( * ) Notice: Subject to any disclaimer, the term of this patent is extended or adjusted under 35 U.S.C. 154(b) by 1143 days.

(21) Appl. No.: 16/057,969

(22) Filed: Aug. 8, 2018

(65) Prior Publication Data

US 2020/0046384 A1    Feb. 13, 2020

(51) Int. Cl.
| | | |
|---|---|---|
| *A61M 5/32* | (2006.01) | |
| *A61B 17/22* | (2006.01) | |
| *A61F 5/441* | (2006.01) | |
| *A61M 3/02* | (2006.01) | |
| *A61B 10/00* | (2006.01) | |
| *A61M 5/14* | (2006.01) | |
| *A61M 5/31* | (2006.01) | |
| *A61M 5/00* | (2006.01) | |
| *A61M 1/00* | (2006.01) | |
| *A61M 31/00* | (2006.01) | |
| *A61M 27/00* | (2006.01) | |
| *A61F 5/44* | (2006.01) | |

(Continued)

(52) U.S. Cl.
CPC .......... *A61B 17/22* (2013.01); *A61B 10/0038* (2013.01); *A61F 5/441* (2013.01); *A61M 3/0295* (2013.01); *A61B 2017/00991* (2013.01); *A61B 2017/22037* (2013.01); *A61M 2025/1061* (2013.01); *A61M 2202/068* (2013.01)

(58) Field of Classification Search
CPC A61M 5/32; A61M 5/14; A61M 5/31; A61M 5/00; A61M 1/00; A61M 31/00; A61M 27/00; A61M 3/0295; A61M 2025/1061; A61M 2202/068; A61F 5/44; A61F 2/00; A61F 2/02; A61B 2017/00991; A61B 2017/22037
See application file for complete search history.

(56) References Cited

U.S. PATENT DOCUMENTS

| | | |
|---|---|---|
| 2,545,796 A | 3/1951 | Scheiwer |
| 2,854,259 A | 9/1958 | Clark |

(Continued)

FOREIGN PATENT DOCUMENTS

CA    1084551    8/1980

OTHER PUBLICATIONS

PCT International Patent Application No. PCT/US18/21467; International Search Report and Written Opinion of the International Searching Authority dated Jun. 1, 2018, 9 pages.

(Continued)

*Primary Examiner* — Tatyana Zalukaeva
*Assistant Examiner* — Ilya Y Treyger
(74) *Attorney, Agent, or Firm* — Craig R. Miles; CR Miles P.C.

(57) ABSTRACT

A stool management system having a tubular body including a first end section disposable in a rectum of a patient and a second end section including a first connector which detachably mates with a second connector coupled to a collection container which receives waste matter passed through the tubular body from the bowel of the patient.

24 Claims, 17 Drawing Sheets

(51) Int. Cl.
    *A61F 2/00*           (2006.01)
    *A61B 17/00*         (2006.01)
    *A61M 25/10*        (2013.01)

(56) References Cited

U.S. PATENT DOCUMENTS

| | | |
|---|---|---|
| 4,676,778 A | 6/1987 | Nelson, Jr. |
| 4,733,692 A | 3/1988 | Kotake et al. |
| 4,819,692 A | 4/1989 | Olson et al. |
| 7,147,627 B2 | 12/2006 | Kim et al. |
| 7,722,583 B2 | 5/2010 | Kim et al. |
| 8,016,816 B2 | 9/2011 | Gregory |
| 8,075,540 B2 | 12/2011 | von Dyck et al. |
| 8,323,255 B2 | 12/2012 | Martino et al. |
| 8,926,577 B2 | 1/2015 | Nishtala et al. |
| 9,463,110 B2 | 10/2016 | Nishtala et al. |
| 2004/0079423 A1 | 4/2004 | Mikiya et al. |
| 2009/0030387 A1 | 1/2009 | Kim et al. |
| 2010/0211050 A1* | 8/2010 | Luther .............. A61M 25/0017 604/544 |
| 2011/0127767 A1 | 6/2011 | Wicks et al. |
| 2011/0295236 A1 | 12/2011 | Gregory |
| 2015/0076815 A1 | 3/2015 | Lombardi et al. |
| 2016/0047503 A1 | 2/2016 | Ballard et al. |
| 2017/0020711 A1 | 1/2017 | Nishtala et al. |
| 2017/0203089 A1 | 7/2017 | Ciccone et al. |

OTHER PUBLICATIONS

Eldon James. Introducing SeriesLock™ the Spring-Free Flow Path Quick Disconnect Coupler (with video). Website, https://www.eldonjames.com/serieslock-quick-disconnect-coupler/, originally downloaded Jun. 6, 2018, 5 pages.

\* cited by examiner

STOOL MANAGEMENT SYSTEM

I. FIELD OF THE INVENTION

A stool management system having a tubular body including a first end section adapted to dispose in a rectal vault and a second end section including a first connector which detachably mates with a second connector coupled to a collection container which receives waste matter passed through the tubular body.

II. BACKGROUND OF THE INVENTION

Many circumstances may result in an individual becoming incontinent for an extended period of time. Examples of such circumstances include head or spinal cord trauma, disabling strokes, microbial caused illness, broken lower limbs or pelvic bones, digestive disorders, intensive care stays, and as side effects of administration of various pharmaceuticals. Thus, there is a great need for devices and methods to transfer waste matter from the bowel of incontinent individuals to a collection container without, or with reduced contact, with the individual or caregiver.

III. SUMMARY OF THE INVENTION

Accordingly, the instant stool management system includes features that provide advantages in the care of incontinent individuals for diversion of waste matter from the bowel to a collection container which minimizes contact of the waste matter with the individual or caregiver.

A broad object of particular embodiments of the invention can be to provide a tubular body having a first end section adapted to dispose in a rectal vault of an individual which affords an inflatable cuff disposed about a tubular strut. Embodiments of the tubular strut, upon placement of the inflatable cuff in the rectal vault, affords sufficient stiffness in a transsphincteric region of the tubular strut to resist collapse or substantial deformation and to resist expulsion of the inflatable cuff from the rectal vault. In particular embodiments, the portion of tubular strut supporting the inflatable cuff can increase in diameter approaching the retention cuff open end to resist expulsion from the rectal vault, while in other embodiments, can taper approaching the retention cuff open end with corresponding increase in the retention cuff wall thickness proximate the open end, thereby affording the advantage of allowing the thicker portion of the retention cuff wall to fold adjacent the tapered portion of the tubular strut to reduce volume of the end section in the rest condition of the retention cuff for more ready insertion through the anal canal and the thicker wall in the inflated condition of the retention cuff resists deformation which reduces likelihood of expulsion of the retention cuff from the anal canal.

Another broad object of particular embodiments of the invention can be to provide a tubular body including a union section between upper and lower tubular body sections. In particular embodiments, the union section can include and an occlusion balloon which can transition between a deflated condition to an inflated condition to occlude the tubular body lumen to prohibit or minimize the transfer of waste matter through the tubular body and conferring the advantages of positioning waste matter for sampling through a releasably sealable sample port disposed in the union section, allowing replacement of the collection container without concurrently handling of waste material flow, or to retain medicaments within the rectal vault.

Another broad object of particular embodiments of the invention can be to provide a tubular body including a second end section having a first connector which detachably mates with a second connector. In particular embodiments, the first connector can include a vent element which transitions from a vent open condition to a vent closed condition, when the first connector detaches from the second connector, which block transfer of waste through the first connector. In particular embodiments, the vent element can further include a porous plug which selectively blocks the flow of waste solids but allows the release of waste gas. In particular embodiments, the second connector can include a seal element which transitions from a seal closed condition to a seal open condition upon attachment of the first connector to the second connector. In further particular embodiments, the seal element can include resiliently flexible wipers, which upon attachment of the first and second connectors, flex to become disposed on the external surface of the first connector, and upon detachment the resiliently flexible wipers can scrape waste matter from the external surface of the first connector toward the lumen of the second connector.

Another broad object of particular embodiments of the invention can be to provide an antimicrobial tubular body, or antimicrobial layer overlaying the tubular body, which includes an antimicrobial agent. The antimicrobial agent can be in amounts effective to kill or inhibit growth of microorganisms in contact with the antimicrobial layer.

Naturally, further objects of the invention are disclosed throughout other areas of the specification, drawings, photographs, and claims.

IV. BRIEF DESCRIPTION OF THE DRAWINGS

V. DETAILED DESCRIPTION OF THE INVENTION

Figure 1:
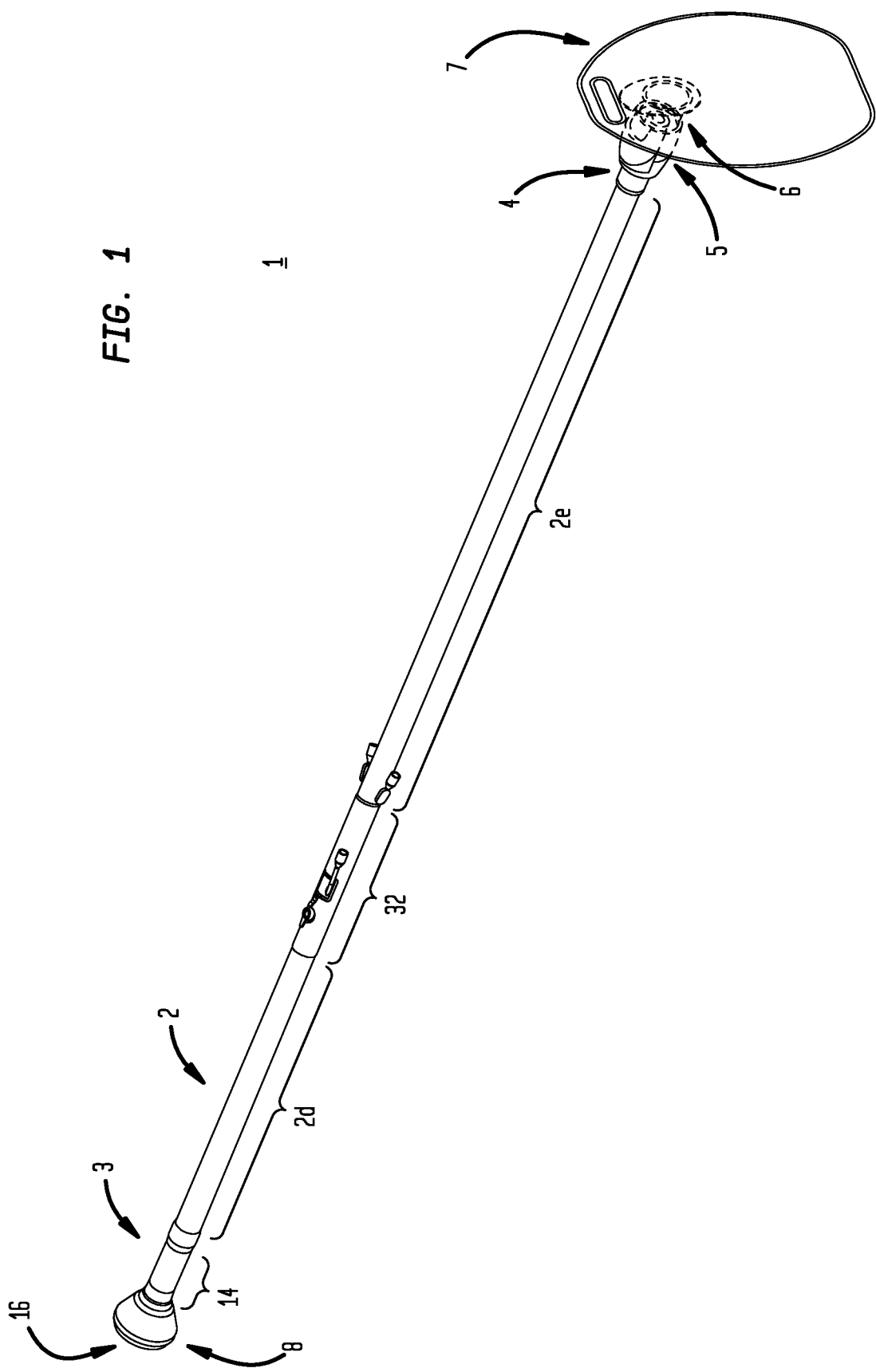
FIG. 1 is a perspective view of an embodiment of a stool management system.
Figure 2:
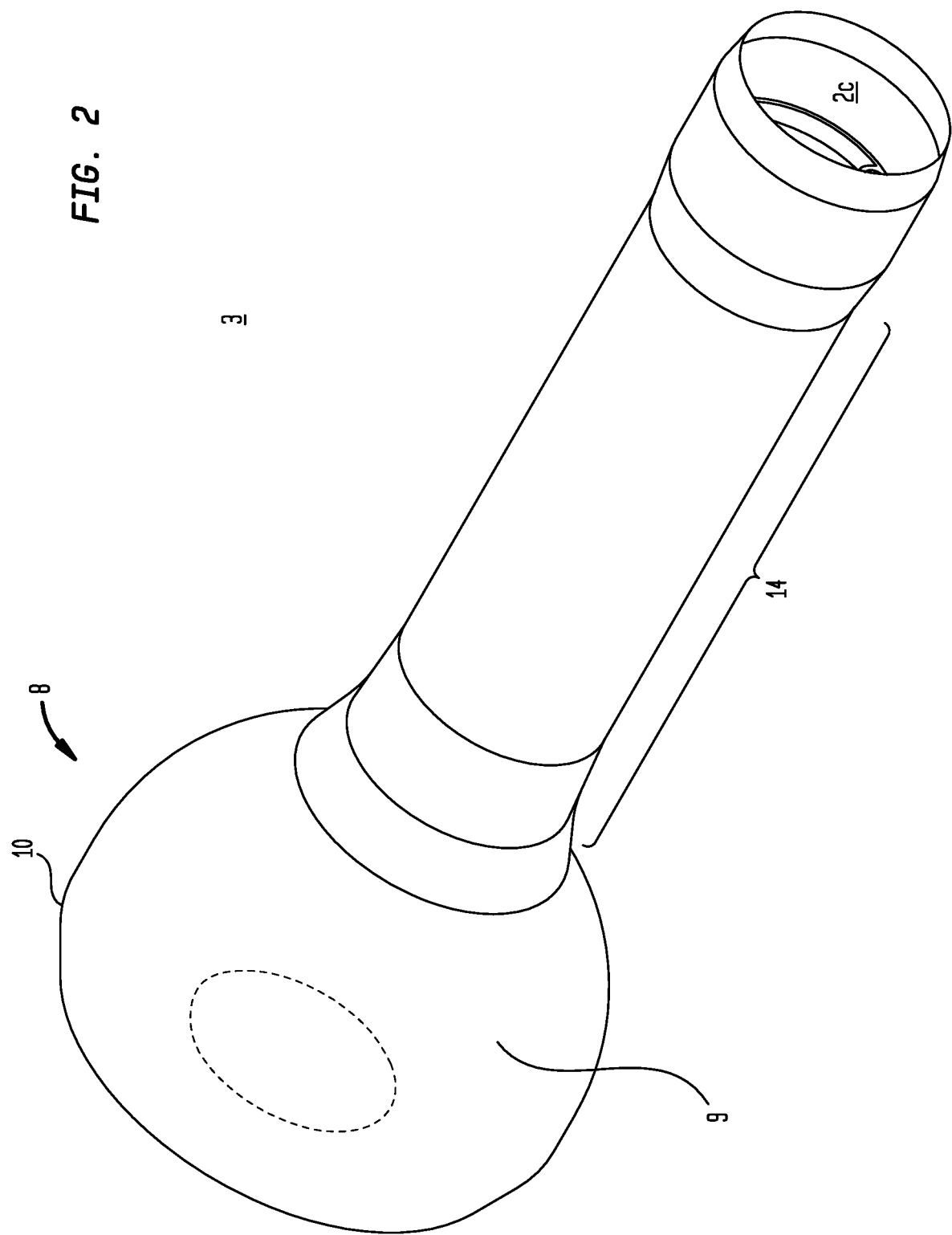
FIG. 2 is a perspective view of an embodiment of first end section of the stool management system.
Figure 3:
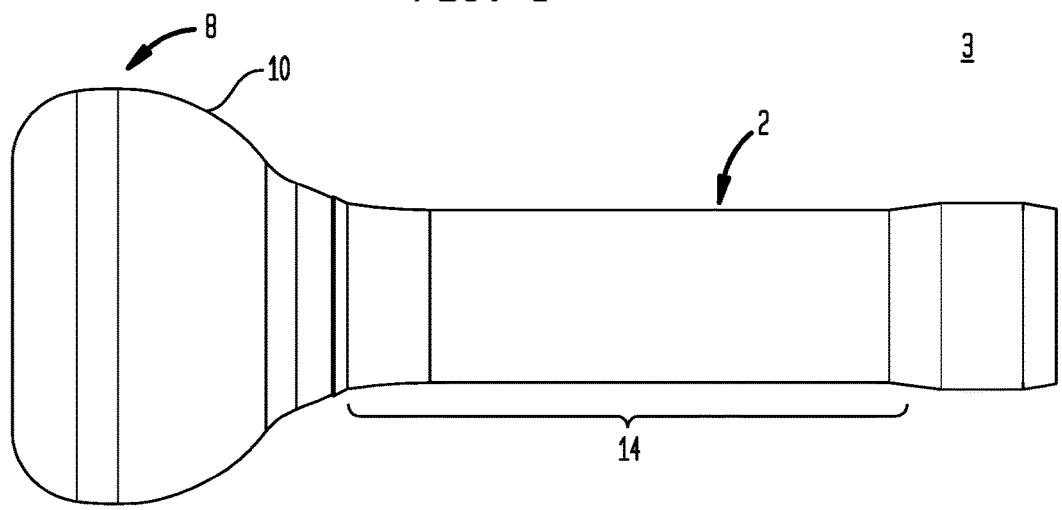
FIG. 3 is first side view of the first end section of the stool management system.

Referring generally to FIGS. 1 through 32, particular embodiments of a stool management system (1) can include one or more of: a tubular body (2) including a first end section (3) which can be disposed in a rectal vault of an individual and a second end section (4) including a first connector (5) which detachably mates with a second connector (6) coupled to a collection container (7). The tubular body (2) having a tubular body internal surface (2a) defining a tubular body lumen (2c).

Now referring primarily to FIGS. 2 through 7, in particular embodiments of the stool management system (1) the first end section (3) includes a retention cuff (8) disposed about a tubular strut (9). The retention cuff (8) includes a retention cuff wall (10) defining an interior space (11) in which a fluid (12) can collect causing transition of the retention cuff (8) from a rest volume (8a) (as shown in broken line in the example of FIG. 4) to an inflated volume (8b) (as shown in solid line in the example of FIG. 4). The retention cuff (8) in the rest volume (8a) can be passed through the anal canal and disposed in a rectal vault of an individual disposing a tubular transsphincteric region (14) of the tubular body (2) in the anal canal of the individual. The anal canal can be distinguished from the rectum because of the transition of the internal surface from a mucous membrane layer to an ectodermal layer (skin like tissue). Typically, the anal canal has a length of about 2.5 to about 4 cm (about 1 inch to about 1.5 inches). External and internal anal sphincters wrap around the anal canal and contract during rest and sleep to prevent discharge of waste matter (15) from the anus.

Again, referring primarily to FIGS. 2 through 7, the tubular strut (9) can, but need not necessarily, can increase in diameter approaching the retention cuff open end (16) which receives waste matter (15) from the rectal vault into the tubular body lumen (2c) of the tubular body (2). The increased diameter of the tubular strut (9) can function to resist expulsion of the retention cuff (8) from the rectal vault, while in other embodiments, the tubular strut (9) can, but need not necessarily, taper approaching the retention cuff open end (16). A taper in the tubular strut (9) can confer an advantage of allowing the retention cuff wall (10) to fold upon the taper of the tubular strut (9) to present a rest volume (8a) of the retention cuff (8) at the retention cuff open end (16) with further reduced volume for more ready insertion into and through the anal canal of the individual.

The tubular strut (9) and the tubular transsphincteric region (14) can be formed of a material having a durometer hardness sufficient to avoid collapse and subsequent blocking of waste matter (15) outflow from the rectal vault. Examples of suitable materials from which the tubular strut (9) and the tubular transsphincteric region (14) can be formed include or consist of: polyurethane, silicone rubber, natural rubber, synthetic rubber, latex, polydimethylsiloxane, fumed silica, polyvinyl chloride, and combinations thereof. As to particular embodiments, the durometer hardness of the tubular strut (9) or the tubular transsphincteric region (14), or both, can occur in a range of about 40 A Shore hardness to about 90 A Shore hardness; although the durometer hardness may be different between the tubular strut (9) and the tubular transsphincteric region (14).

In particular embodiments, the retention cuff wall (10) can but need not necessarily, have a retention cuff wall thickness (17) which increases approaching the retention cuff open end (16) of said retention cuff (8). The increasing retention cuff wall thickness (17) can confer an advantage in the inflated volume (8b) of the retention cuff (8) of resisting deformation which reduces likelihood of expulsion of the retention cuff (8) from the anal canal. Examples of suitable materials from which the retention cuff (8) can be formed can include or consist of: polyurethane, silicone rubber, natural rubber, synthetic rubber, latex, polydimethylsiloxane, fumed silica, polyvinyl chloride, and combinations thereof. The durometer hardness of the retention cuff wall (10) can be about 35 A Shore hardness to about 50 A Shore hardness.

Again, referring primarily to FIGS. 2 through 7, the retention cuff (8) can be retained in the rectal vault of the individual by inflation of the retention cuff (8) to the inflated volume (8b). The inflated volume (8b) of the retention cuff (8) can be sufficiently large to prevent expulsion of the retention cuff (8) through the anal canal.

Figure 5:
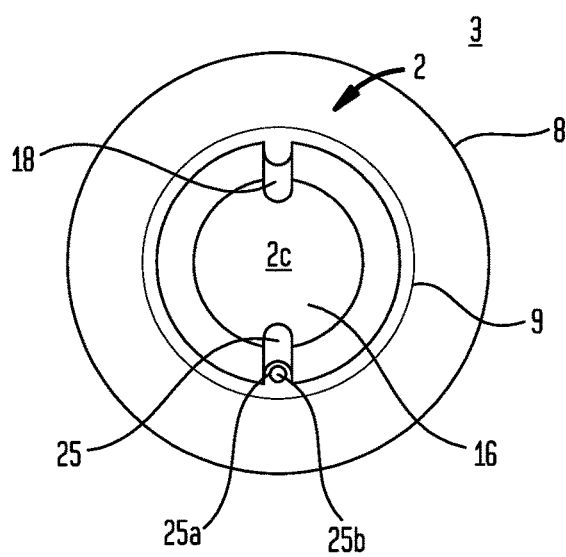
FIG. 5 is a first end view of the first end section of the stool management system.
Figure 6:
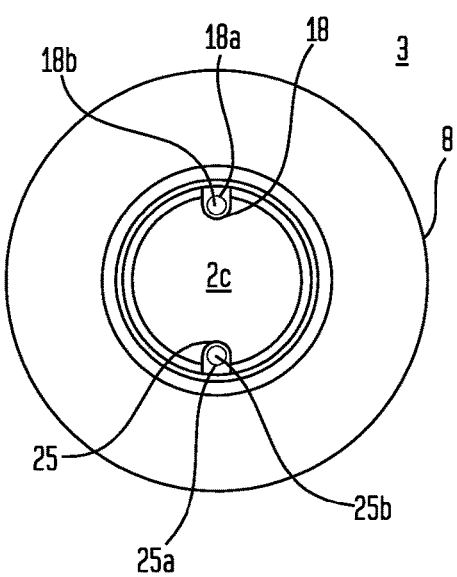
FIG. 6 is a second end view of the first end section of the stool management system.
Figure 7:
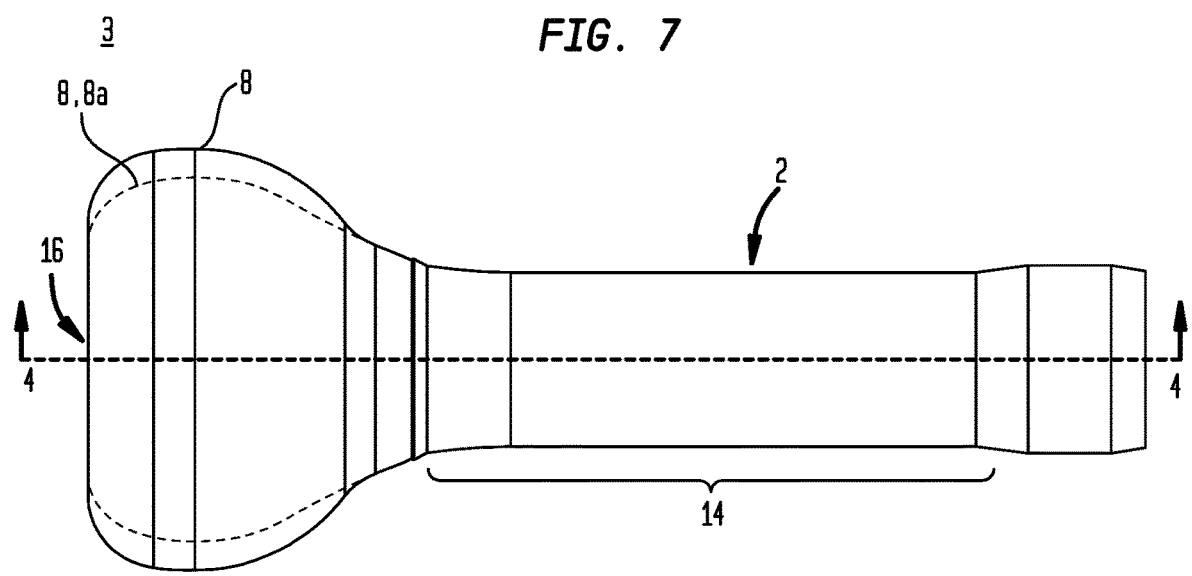
FIG. 7 is a second side view of the first end section of the stool management system.
Figure 11:
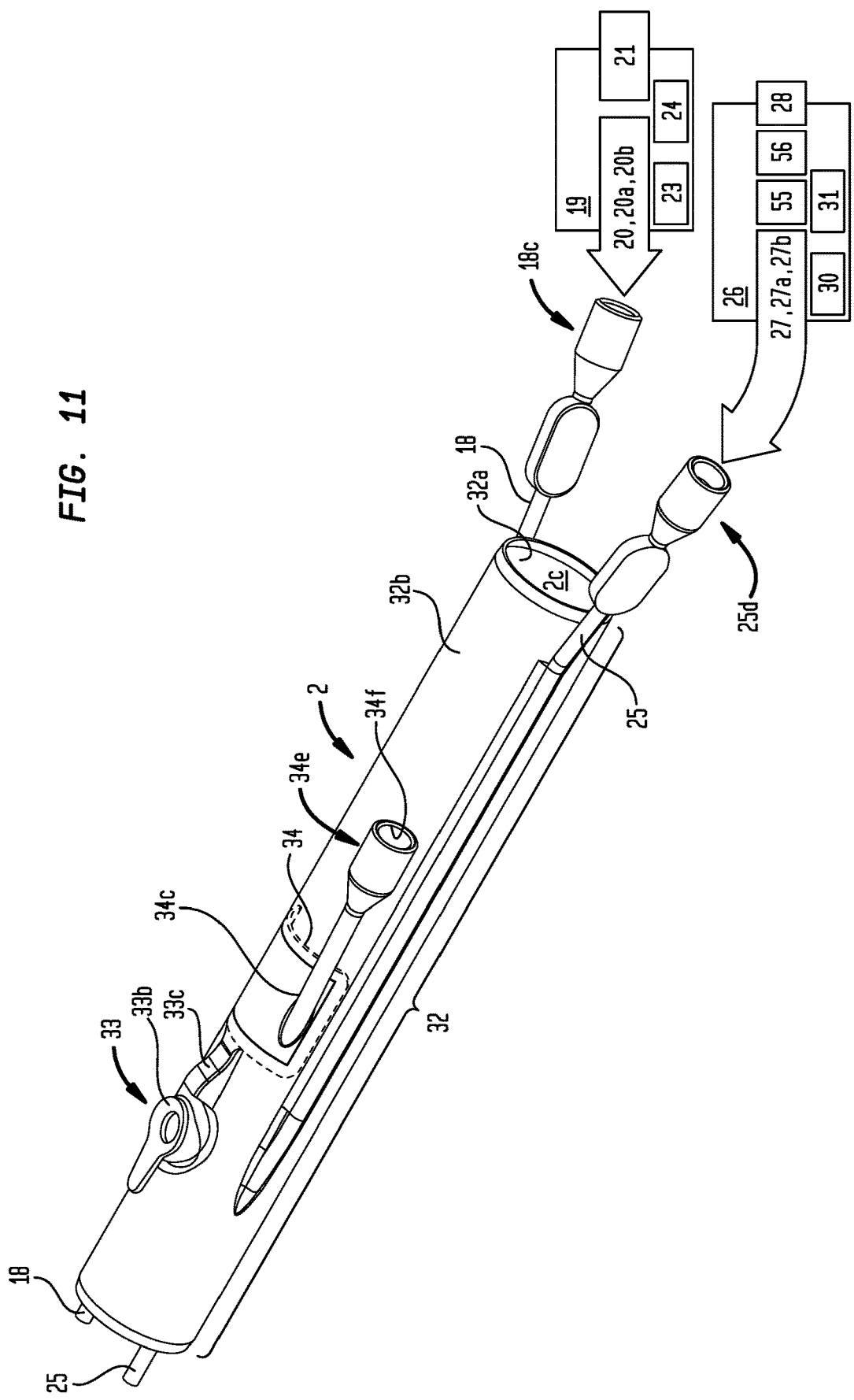
FIG. 11 is a perspective view of a particular embodiment of a union section of the stool management system.
Figure 12:
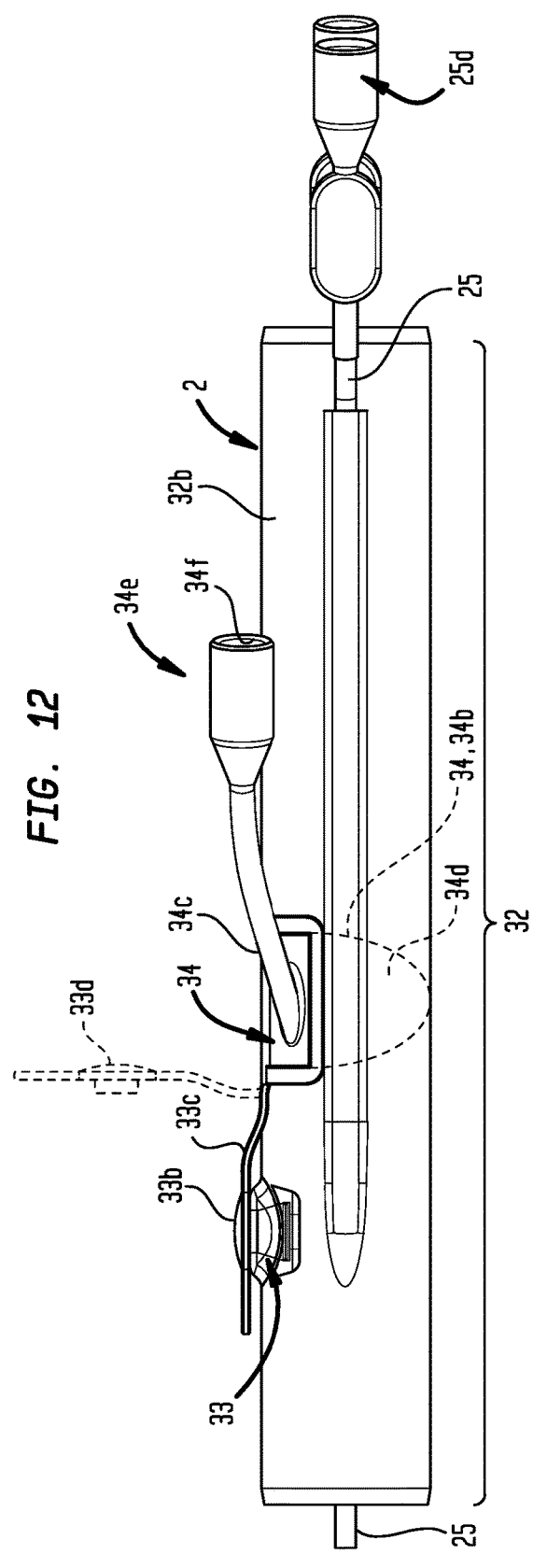
FIG. 12 is side view of the union section of the stool management system.
Figure 13:
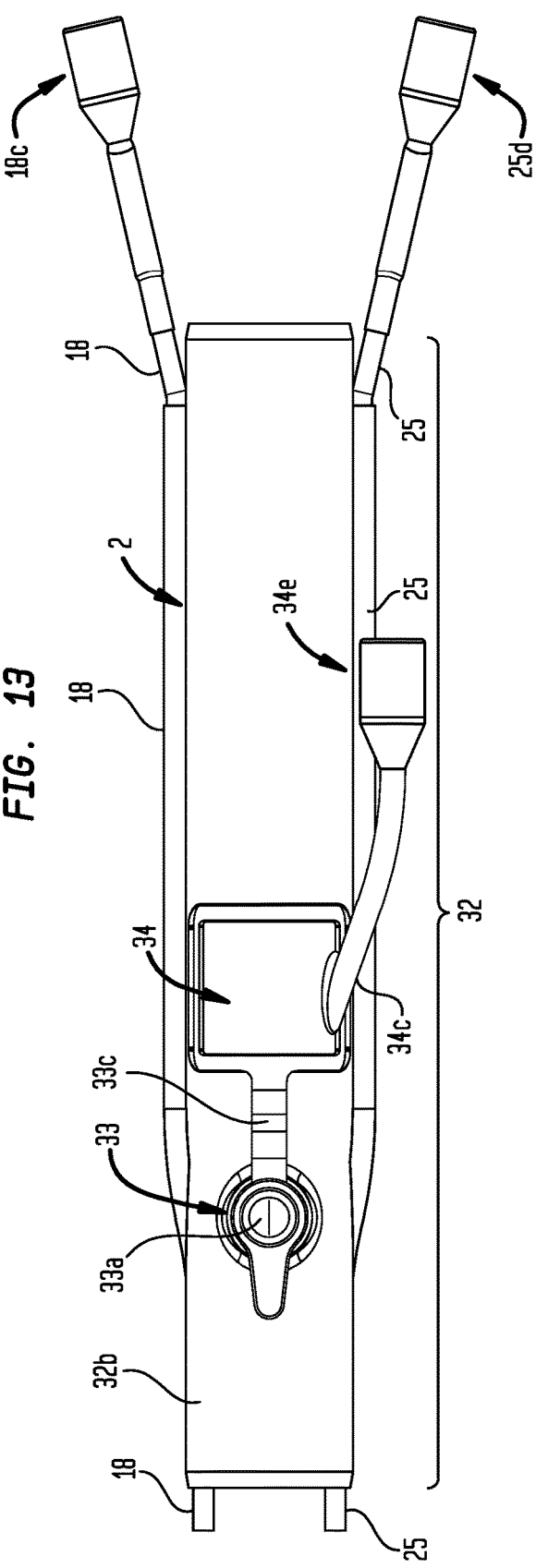
FIG. 13 is top view of the union section of the stool management system.

In particular embodiments, an inflation conduit (18) can be disposed inside of the tubular strut (9). The inflation conduit (18) can have an inflation conduit internal surface (18a) defining an inflation conduit lumen (18b) fluidically coupled to the interior space (11) of the retention cuff (8). In particular embodiments, the inflation conduit (18) can be formed as one piece with the tubular body (2) (as shown in the example of FIGS. 5 and 6). The inflation conduit (18) can extend a distance inside the tubular body lumen (2*c*) of the tubular body (2) and pass through the tubular body (2) to terminate in an inflation port (18*c*) outside of the tubular body (2) (as shown in the example of FIG. 11). In particular embodiments, the inflation port (18*c*) can have an inflation port internal surface (18*d*) configured to mate with an inflation device (19) which channels inflation fluid (20) from a fluid supply (21) into the inflation device (19). The inflation device (19) can, but need not necessarily, include fluid sensors (23) for measuring inflation fluid pressure (20*a*) and inflation fluid flow (20*b*) in the inflation conduit lumen (18), and a controller (24) responsive to the sensors (23) for automatically regulating the inflation fluid pressure (20*a*) and inflation fluid flow (20*b*) to the interior space (11) of the retention cuff (8).

For the purposes of this invention the term "inflation fluid" means a substance able to flow within the inflation conduit lumen (18*b*) and without limitation of the breadth of the foregoing, illustrative examples of a fluid include or consist of: a gas, a mixture of gases, air, a liquid, a mixture of liquids, a substance dissolved in a solvent, a gel, a colloid, water, and combinations thereof.

In particular embodiments, the port internal surface (18*d*) can, but need not necessarily, be configured to receive a Luer taper fitting consistent with an ISO 594 standard or an ISO 80369 standard for medical equipment. Fluid (20) can be introduced into the inflation port (18*c*) under sufficient fluid pressure (20*a*) to generate a fluid flow (20*b*) from the inflation port (18*c*) toward the interior space (11) of the retention cuff (8) to achieve the inflated volume (13*b*) of the retention cuff (8).

Again, primarily referring to FIGS. 2 through 7, in particular embodiments, an irrigation conduit (25) can be disposed within the tubular strut (9). The irrigation conduit (25) can have an irrigation conduit internal surface (25*a*) defining an irrigation lumen (25*b*) having an irrigation lumen open end (25*c*) disposed proximate the retention cuff open end (16). In particular embodiments, the irrigation conduit (25) can be formed as one piece with the tubular body (2) (as shown in the example of FIG. 6). The irrigation conduit (25) can extend a distance inside the tubular body lumen (2*c*) of the tubular body (2) to terminate in an irrigation port (25*d*) outside of the tubular body (2). In particular embodiments, the irrigation port (25*d*) can have an irrigation port internal surface (25*e*) configured to mate with an irrigation device (26) which can channel an irrigation fluid (27) from an irrigation fluid supply (28) into an irrigation device (26). The irrigation device (26) can, but need not necessarily, include irrigation fluid sensors (30) for measuring irrigation fluid pressure (27*a*) and irrigation fluid flow (27*b*) in the irrigation lumen (25*b*), and a controller (31) responsive to the irrigation fluid sensors (30) for automatically regulating the irrigation fluid pressure (30*a*) and irrigation fluid flow (27*b*) toward the irrigation conduit open end (25*c*).

For the purposes of this invention the term "irrigation fluid" means a substance able to flow within the irrigation lumen (25*b*) and without limitation to the breadth of the foregoing, illustrative examples of an irrigation fluid include or consist of: a gas, a mixture of gases, air, a liquid, a mixture of liquids, a substance dissolved in a solvent, a gel, a colloid, water, and combinations thereof.

In particular embodiments, the irrigation port internal surface (25*e*) can, but need not necessarily, be configured to receive a Luer taper fitting consistent with an ISO 594 or an ISO 80369 standard for medical equipment. An irrigation fluid (27) can be introduced into the irrigation port (25*d*) under sufficient irrigation fluid pressure (27*a*) to generate an irrigation fluid flow (27*b*) from the irrigation port (25*d*) to egress from the irrigation conduit open end (25*c*) proximate the retention cuff open end (16) to achieve an irrigation fluid flow (27*c*) from the irrigation conduit open end (25*c*) into the rectal vault.

Figure 4:
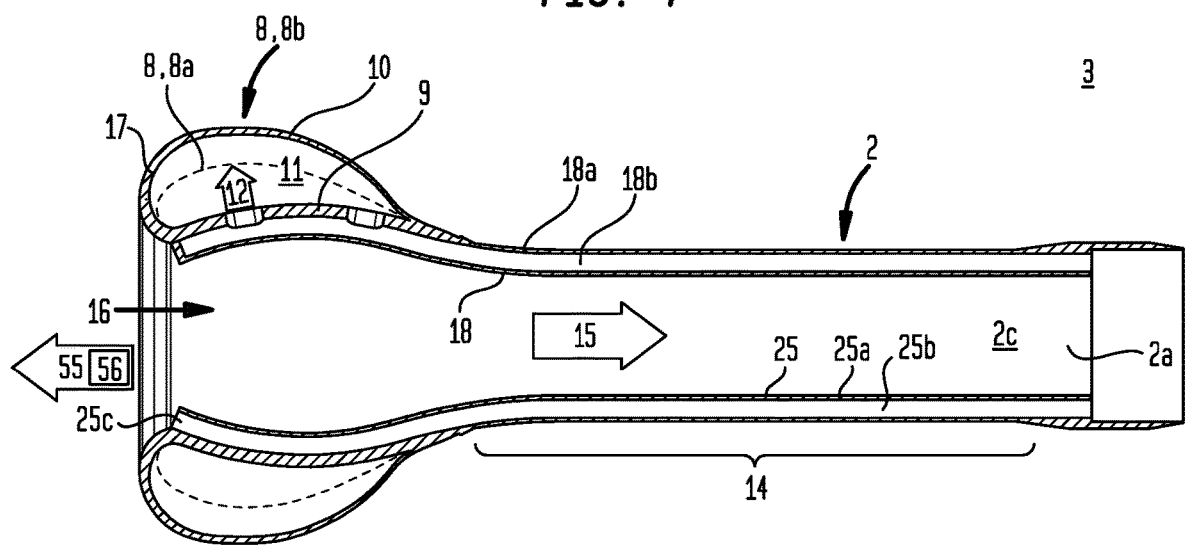
FIG. 4 is a cross section view 4-4 of the first end section of the stool management system.

Now referring generally to FIGS. 1 and 4, waste matter (15) from the bowel or rectal vault can enter the retention cuff open end (16) and pass through the tubular body (2). For the purposes of this invention, the term "waste matter" broadly encompasses any substance or material which passes through the bowel, resides in the rectal vault, or can be introduced into the rectal vault through the irrigation lumen (25*b*), and without limitation to the breadth of the foregoing includes or consists of: solid or semisolid remains of food, fluids, liquids, gases, irrigation fluids, medicaments, or combinations thereof.

The portion of the tubular body (2) connected to the tubular transsphincteric region (14) resides outside of the anus. Examples of a suitable materials from which the tubular body (2) can be formed include or consist of: polyurethane, silicone rubber, natural rubber, synthetic rubber, latex, polydimethylsiloxane, fumed silica, polyvinyl chloride, and combinations thereof. The durometer hardness of the tubular body (2) can be between about 35 A Shore hardness to about 50 A Shore hardness; although durometer hardness can be a greater or lesser Shore hardness depending on the application.

Now referring primarily to FIGS. 1 and 11 through 15, in particular embodiments, the tubular body (2) can include a union section (32) disposed between an upper tubular body section (2*d*) connected to the retention cuff (8) and a lower tubular section (2*e*) connected to the first connector (5) the combination defining the tubular lumen (2*c*). As to these particular embodiments, the upper and lower tubular sections (2*d*)(2*e*) can include or consist of: polyurethane, silicone rubber, natural rubber, synthetic rubber, latex, polydimethylsiloxane, fumed silica, polyvinyl chloride, and combinations thereof. The durometer hardness of the upper and lower tubular sections (2*d*)(2*e*) can be about 35 A Shore hardness to about 50 A Shore hardness; although durometer hardness can be a greater or lesser Shore hardness depending on the application. The union section (32) can be formed from a moldable or injection moldable material including or consisting of: acrylonitrile butadiene styrene, polypropylene, polyoxmethylene, polycarbonate, polyvinylchloride, chitosan, poly (lactide-co-glycolide), and polymethyl methacrylate, nylon, styrene, polyetherimide, urethane dimethacrylate, triethylene glycol dimethacrylate, and combinations thereof.

Figure 8:
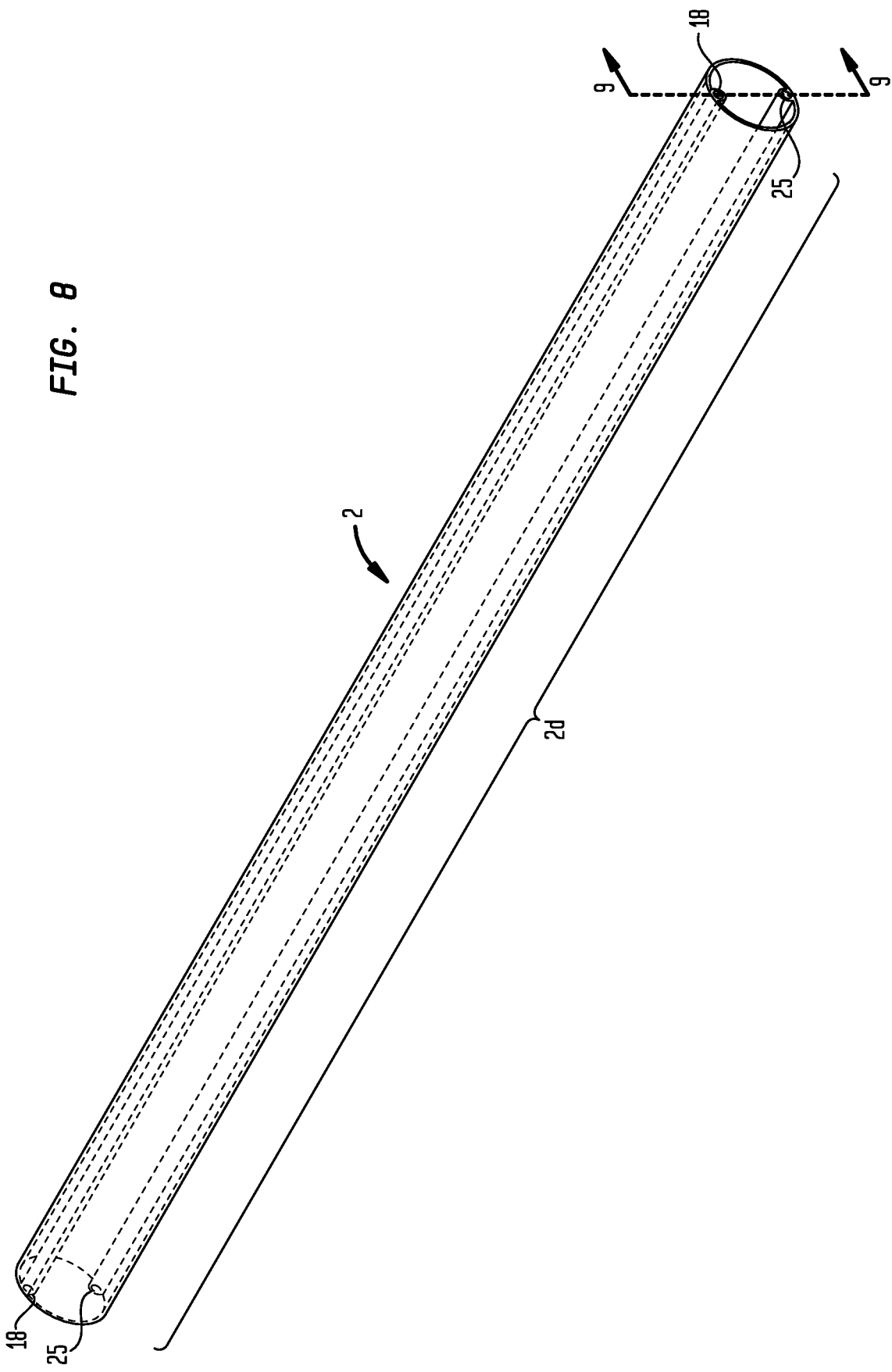
FIG. 8 is a perspective view of a particular embodiment of an upper tubular body section of the stool management system.
Figure 9:
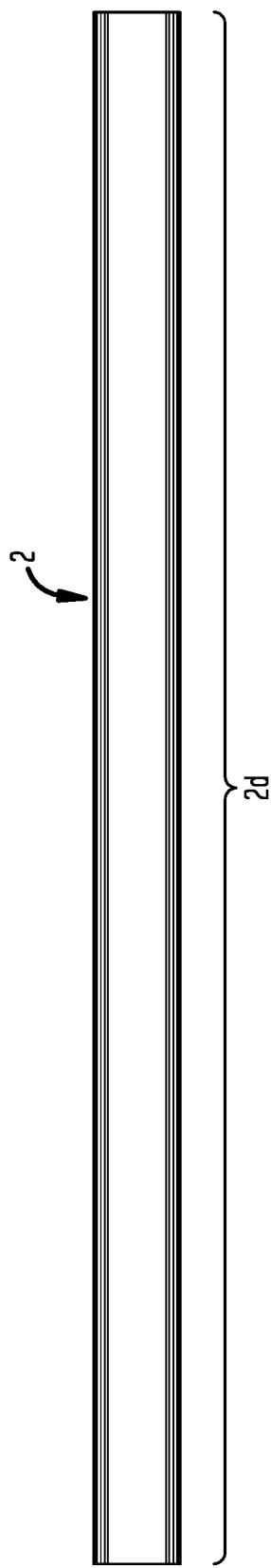
FIG. 9 is a cross section view 9-9 of the upper tubular body section of the stool management system.
Figure 10:
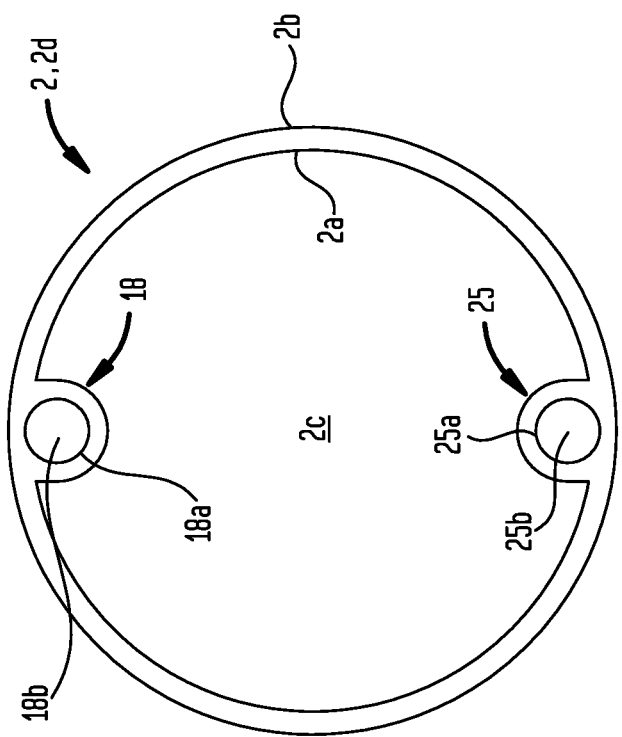
FIG. 10 is an end view the upper tubular body section of the stool management system.
Figure 14:
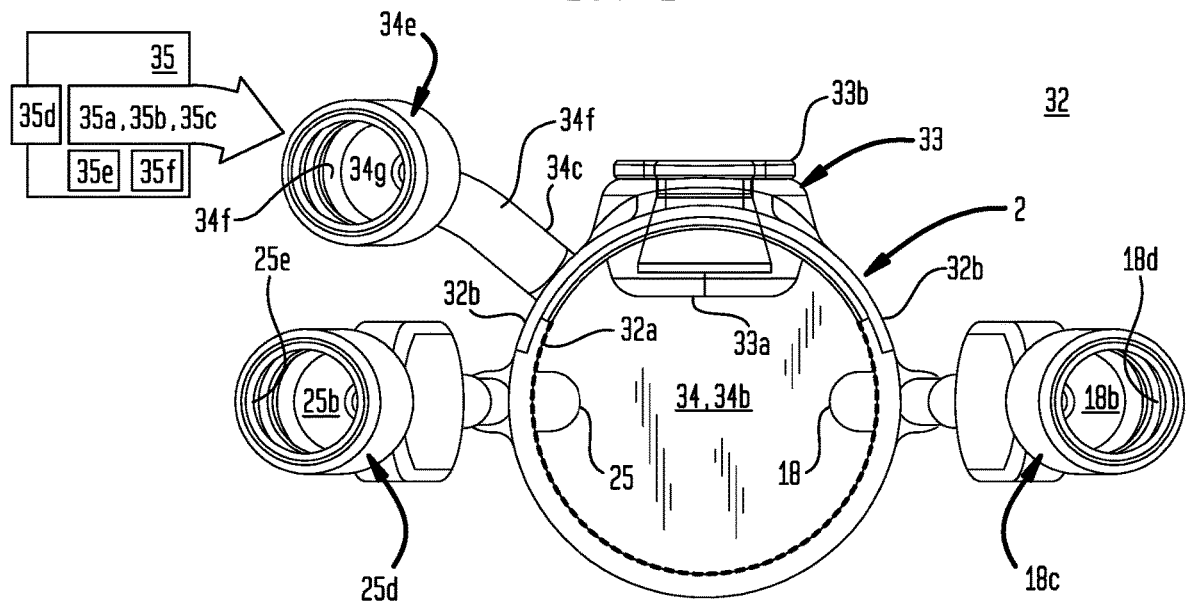
FIG. 14 is a first end view of the union section of the stool management system having an occlusion balloon in the inflated condition.
Figure 15:
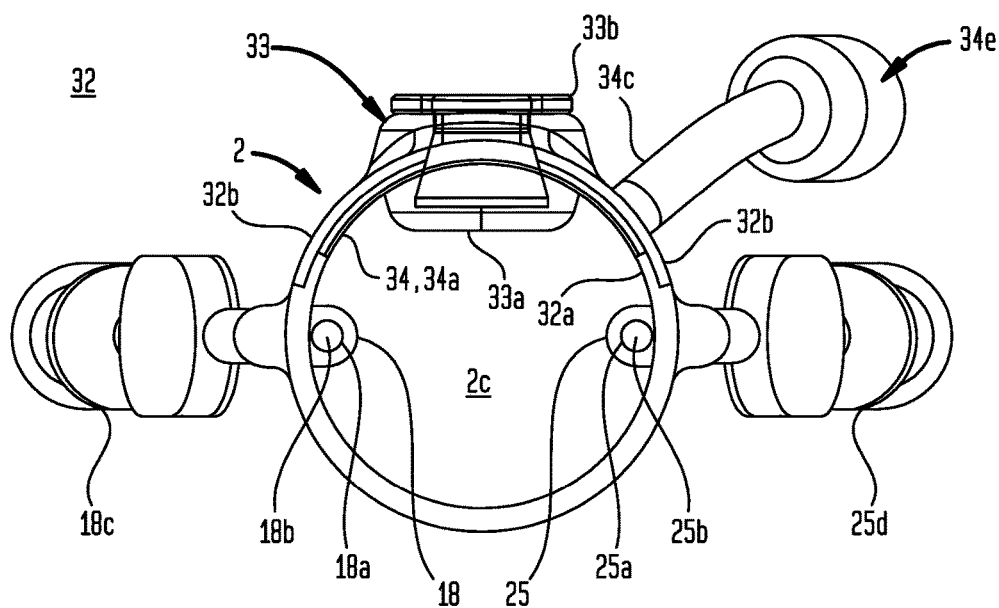
FIG. 15 is a second end view of the union section of the stool management system having the occlusion balloon in the deflated.
Figure 16:
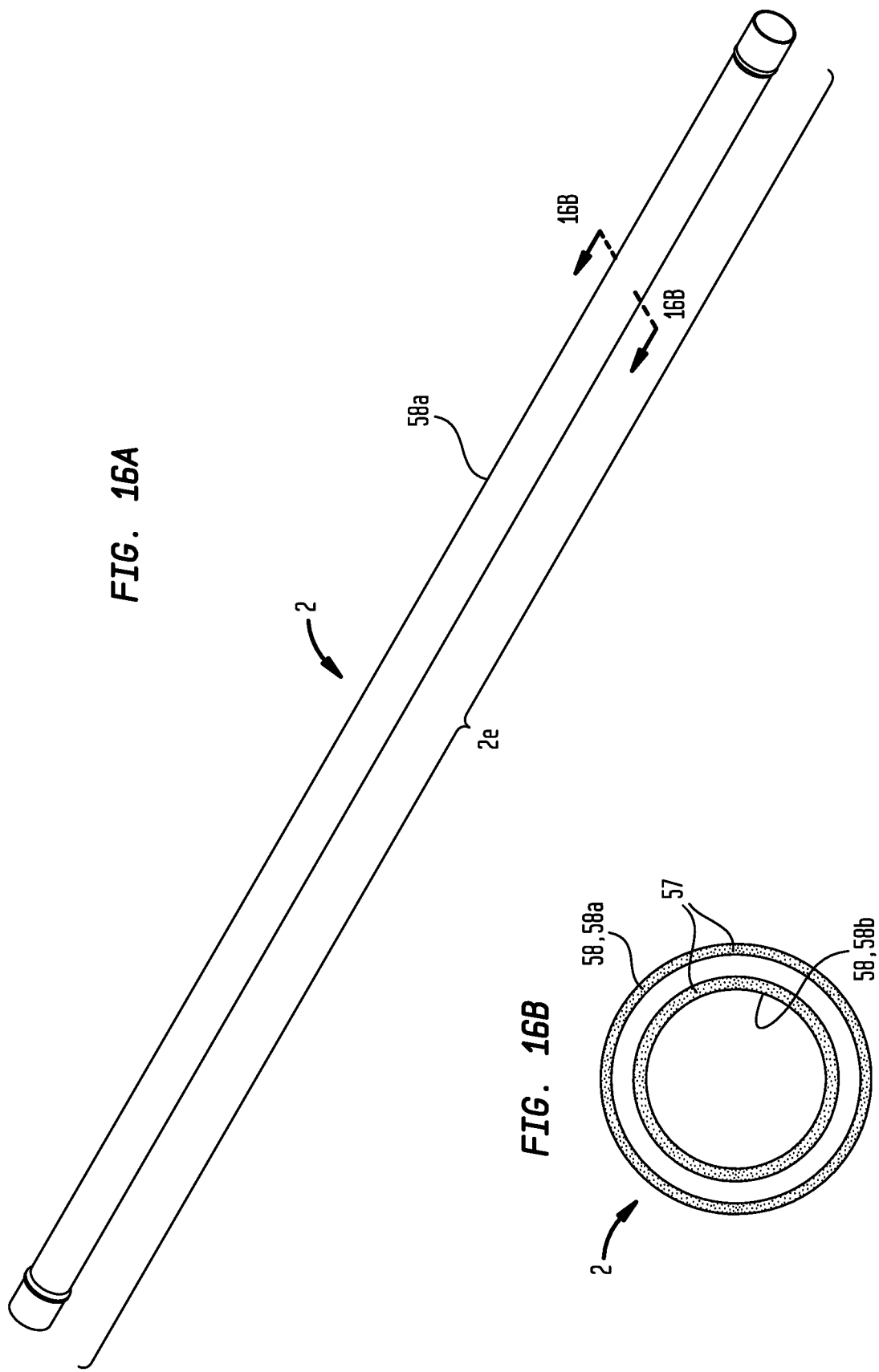
FIG. 16A is a perspective view of a particular embodiment of a lower tubular body section of the stool management system.
FIG. 16B is a cross section view 16B-16B of the particular embodiment of the lower tubular body section shown in FIG. 16A including antimicrobial layers.
Figure 17:
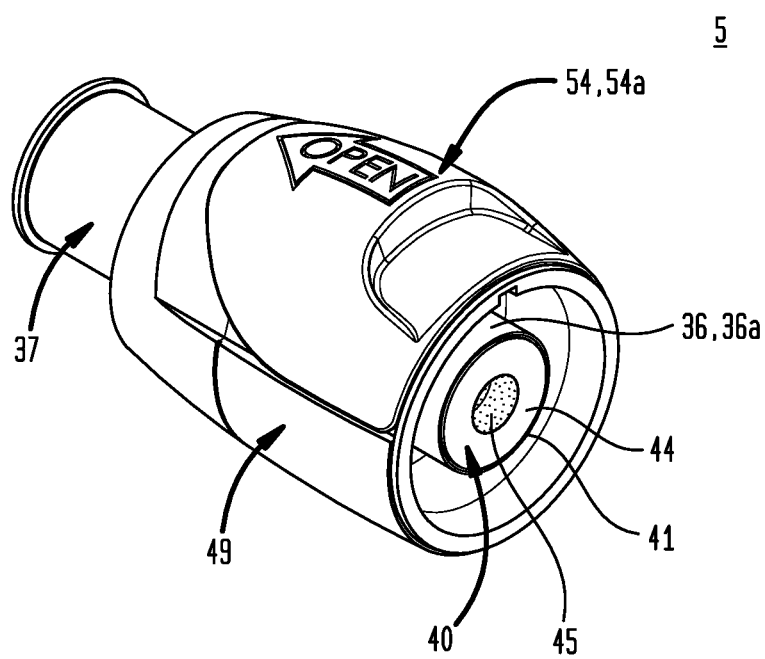
FIG. 17 is a perspective view of a particular embodiment of the first connector of the stool management system.
Figure 18:
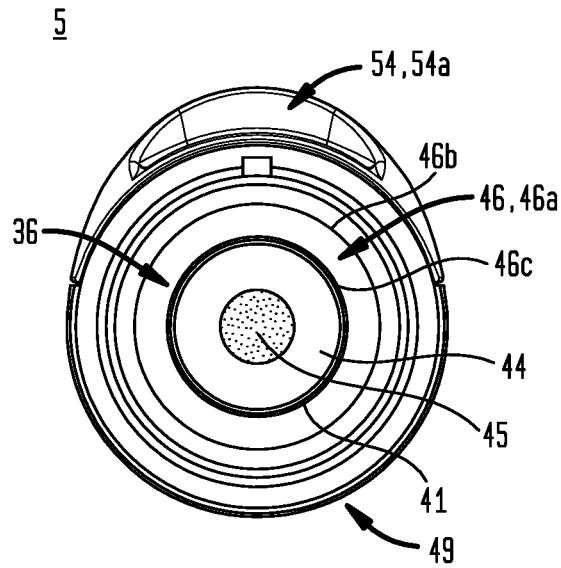
FIG. 18 is a first end view of the first connector of the stool management system.
Figure 19:
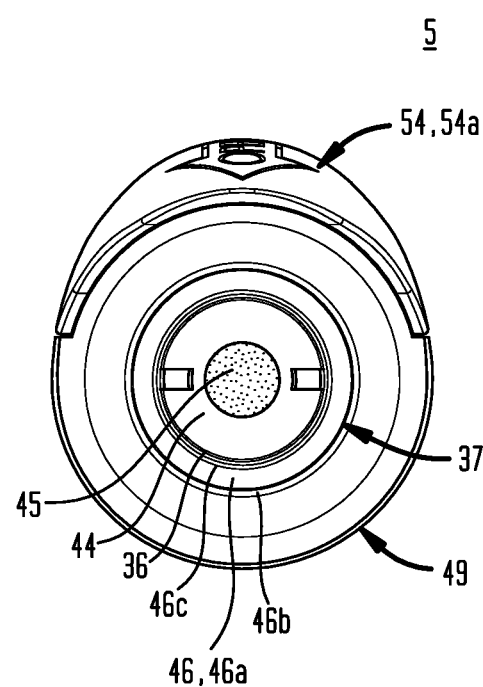
FIG. 19 is a second end view of the first connector of the stool management system.

Now referring primarily to FIGS. 8 through 15, the inflation conduit (18) and the irrigation conduit (25) can optionally extend inside of the upper tubular body section (2*d*) and the union section (32) and each of the inflation conduit (18) and the irrigation conduit (25) can pass through the union section (32) to dispose the inflation port (18*c*) and the irrigation port (25*d*) outside of the union section (32). In particular embodiments, the inflation conduit (18) and irrigation conduit (25) can be formed as one piece with the upper tubular body section (2*d*) (as shown in the examples of FIGS. 8 through 10) or one piece with the union section (32) (as shown in the examples of FIGS. 14 and 15).

Now referring primarily to FIGS. 11 through 15, in particular embodiments, the union section (32) can, but need not necessarily include a sample port (33) including a sample port aperture (33*a*) which extends between the union section internal surface (32a) and a union section external surface (32b) and a sample port aperture closure (33b) which removably seals the sample port aperture (33a). As shown in the illustrative examples, of FIGS. 11 through 13, the sample port aperture closure (33b) can further include a closure tether (33c) which tethers the sample port aperture closure (33b) to the union section external surface (32b). The sample port (33b) can be disposed in the sample port open condition (33d) to allow sampling of the waste matter (15) inside the tubular body passage (2b) the tubular body (2) of the stool management system (1).

Again, referring primarily to FIGS. 11 through 15, in particular embodiments, the union section (32) can, but need not necessarily include, an occlusion balloon (34) which transitions between a deflated condition (34a) adjacent the union internal surface (32a) and an expanded condition (34b) which occludes the tubular body lumen (2c) to block the flow of waste matter (15) through tubular lumen (2c) or allow retention of materials in the rectal vault. As shown in the illustrative examples of FIGS. 11 through 13, the occlusion balloon (34) can further include occlusion balloon conduit (34c) which extends outside of the union section (32) to fluidically couple an occlusion balloon internal volume (34d) with an occlusion balloon port (34e). In particular embodiments, the occlusion balloon port (34e) can have an occlusion balloon port internal surface (34f) (which can, but need not necessarily, be configured to an ISO 594 standard or an ISO 80369) configured to mate with an occlusion balloon inflation device (35) which can channel an occlusion balloon fluid flow (35a) from an occlusion balloon fluid supply (35b) into an occlusion balloon inflation device (35). The occlusion balloon fluid (35a) (can be delivered through the occlusion balloon lumen (34g) to the occlusion balloon internal volume (34d) to generate the expanded condition (34b) and the flow of occlusion balloon fluid (35a) can egress from the occlusion balloon lumen (34c) to result in the deflated condition (34a).

An advantage of embodiments which include an occlusion balloon (34) can be maintenance of substances (55) introduced into the rectal vault whether directly or indirectly through the irrigation conduit (25). The substances (55) introduced into the rectal vault can include, without limitation to the breadth of the foregoing, medicaments (56) including or consisting of: cation exchange resins, such as, kayexalate (sodium polystyrene sulfonate, SPS); antibiotics, such as, vancomycin, rifaximin, or fidaxomicin; laxatives, such as, lactulose; antiparasitics, such as, metronidazole; fecal transplants, and combinations thereof.

Now referring primarily to FIGS. 1 and 17 through 32, embodiments can, but do not necessarily include, a first connector (5) coupled to the second end section (4) of the tubular body (2) and a second connector (6) coupled to the collection container (7). The first and second connectors (5)(6) matingly engage to releasably join the second end section (4) of the tubular body (2) to the collection container (7). Now referring primarily to FIGS. 23 and 24, the first connector (5) includes a first tubular portion (36) which can be slidingly telescopingly engaged to a second tubular portion (37). The second connector (6) includes a tubular member (38). The first tubular portion (36) of the first connector (5) can insertingly engage the tubular member (38) of the second connector (6). The first tubular portion (37) of the first connector (5) inserted within the tubular member (38) of the second connector (6) transitions from an extended condition (36a) (as shown solid object line of FIGS. 23 and 24) toward a retracted condition (36b) (as shown in solid object line of FIG. 32). In particular embodiments, a first tubular portion bias element (39) biases movement of the first tubular portion (36) toward the extended condition (36a). In the illustrative embodiments of FIGS. 23 and 24 the bias element (39) takes the form of a helical compression spring (39a) wound about the second tubular portion (37) of the first connector (5). However, this is not intended to preclude other forms of the bias element (39) such as compressible elastomers, resiliently flexible rods, blades, leaves, or the like.

Figure 23:
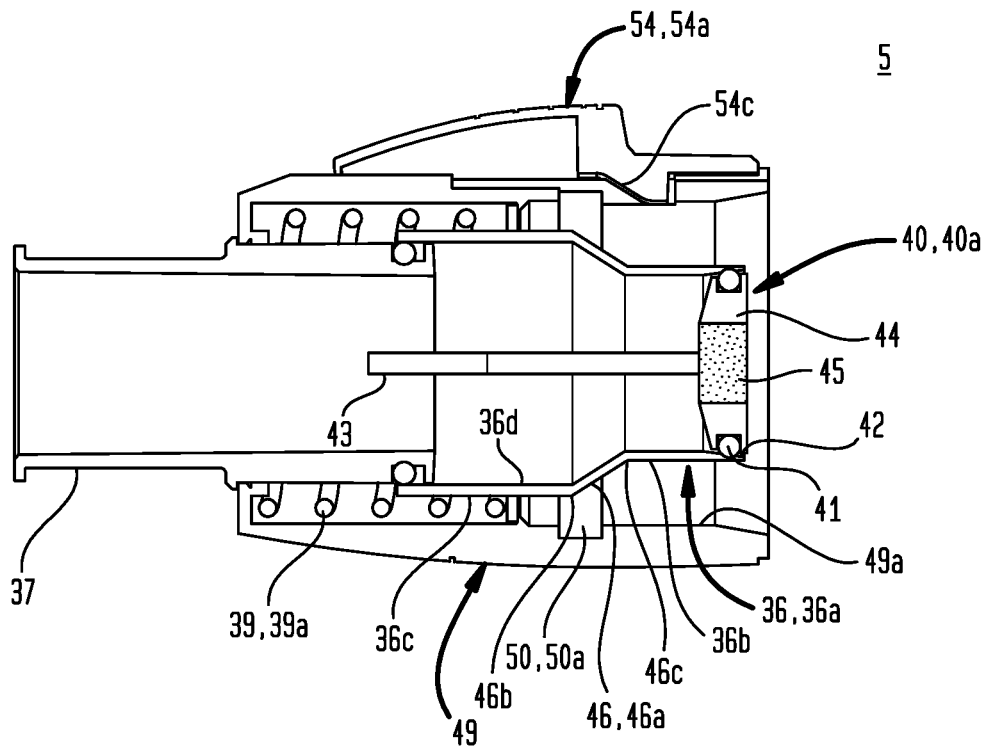
FIG. 23 is cross section view 23-23 of the first connector of the stool management system.
Figure 24:
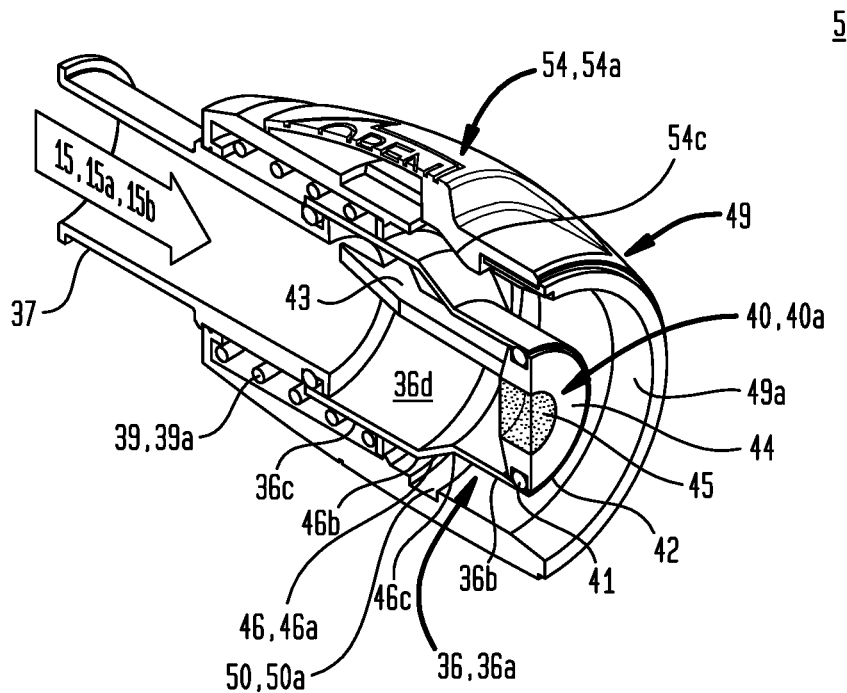
FIG. 24 is cross section view 24-24 of the first connector of the stool management system.

Again, referring primarily to FIGS. 23 and 24, particular embodiments can, but need not necessarily include, a vent element (40) which engages the first tubular portion (36) in the extended condition (36a) to close the tubular body lumen (2c) through the first connector (5). The vent element (40) can be in the form of a disk, and as to particular embodiments, can further include an annular vent seal (41) circumferentially disposed about the vent element periphery (42). A vent element support (43) can extend from the second tubular portion (37) to the vent element (40) to maintain the vent element (40) in fixed spatial relation to the second tubular portion (37) and variable spatial relation to the first tubular portion (36). As the first tubular portion (36) transitions toward the retracted condition (36b) the vent element (40) transitions from a vent closed condition (40a) to a vent open condition (40b). Conversely, as the first tubular portion (36) transitions toward the extended condition (36a) the vent element (40) transitions from the vent open condition (40b) to the vent closed condition (40a). In particular embodiments, the vent element (40) includes an annular peripheral margin (44) disposed about a porous plug (45). The porous plug (45) allows passage of waste matter gas (15a) from within the tubular body lumen (2c) in the vent closed condition (40a), and as to particular embodiments, the porous plug (45) can concurrently prohibit or reduce the flow of solid or liquid waste matter (15b) within the tubular body lumen (2c).

Now referring primarily to FIGS. 23 through 31, in particular embodiments, the first tubular portion (36) of the first connector (5) can further include an abutment element (46) disposed on the first tubular portion external surface (36c). In particular embodiments, the abutment element (46) can comprise a truncated cone (46a) which couples a greater diameter end (46b) to a lesser diameter end (46c) of the first tubular portion (36); however, this example is not intended to obviate other embodiments of the abutment element (46) which can be any feature that extends outward of the first tubular portion external surface (36c).

Again, referring primarily to FIGS. 23 through 31, the second connector (6) can further include an arrest element (47) coupled to the tubular member internal surface (38a). In particular embodiments, the arrest element (47) can comprise an annular shoulder (47a) which reduces the open area of the tubular body lumen (2c) through the second connector (6); however, this example is not intended to obviate other embodiments of the arrest element (47) which can be any feature that extends inward of the tubular member internal surface (38a) to engage the abutment element (46) of the first connector (5) inserted within the tubular member (38) of the second connector (6). The lesser diameter end (46c) of the first tubular portion (36) can pass by the arrest element (47) to engage the abutment element (46) with the arrest element (47) causing the first tubular portion (36) of the first connector (5) to transition from an extended condition (36a) toward the retracted condition (36b) concurrent with transition of the vent element (40) from the vent closed condition (40a) toward the vent open condition (40b).

Figure 25:
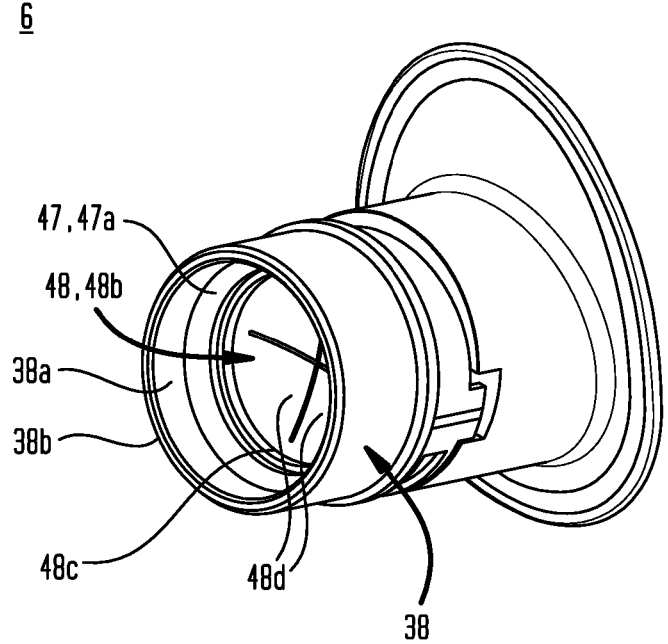
FIG. 25 is a perspective view of a particular embodiment of the second connector of the stool management system.
Figure 26:
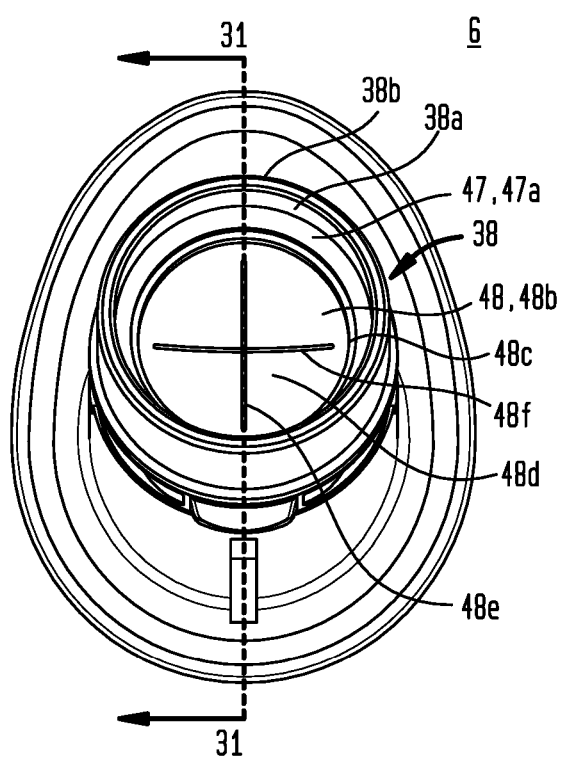
FIG. 26 is a first end view of the second connector of the stool management system.
Figure 27:
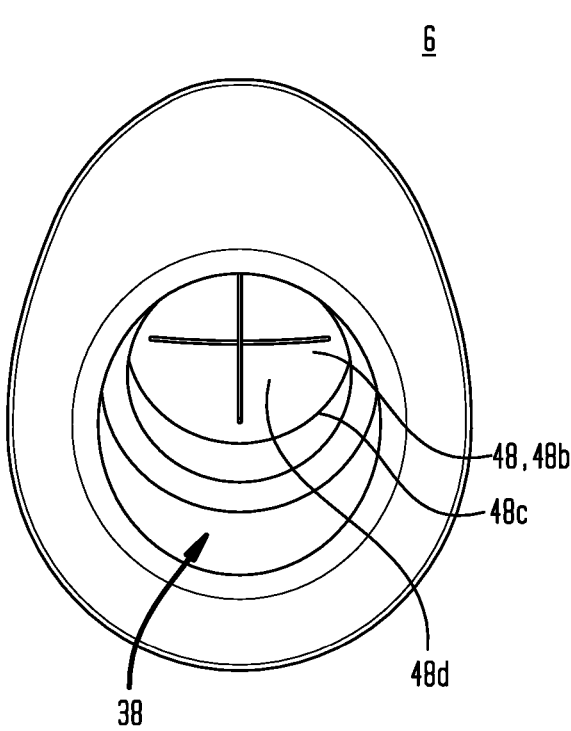
FIG. 27 is a second end view of the second connector of the stool management system.
Figure 32:
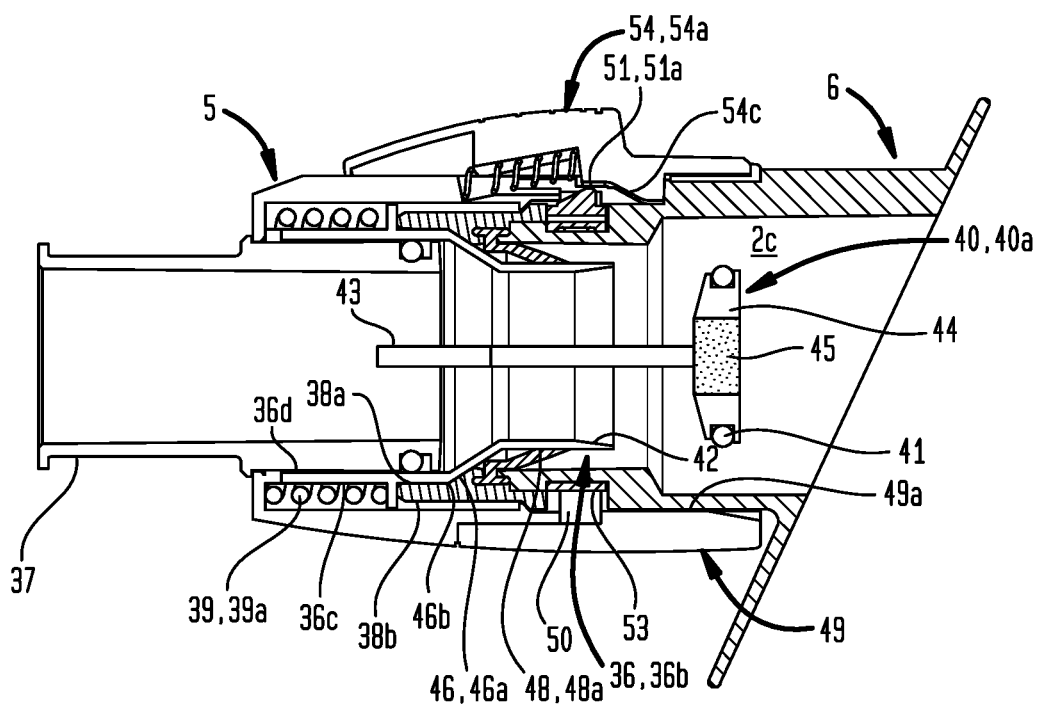
FIG. 32 is cross section 32-32 of the first connector attached to the second connection of the stool management system.
Figure 33:
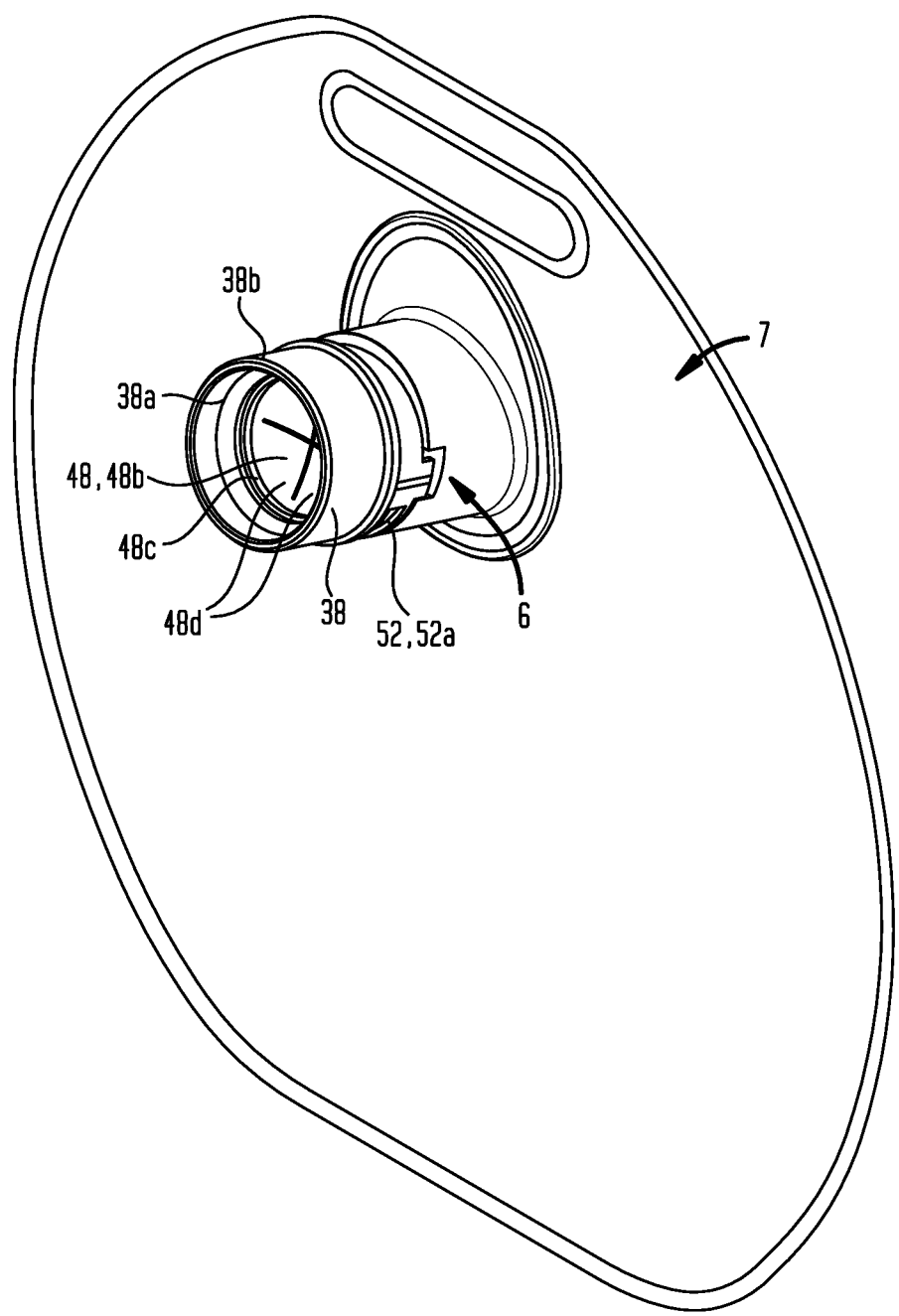
FIG. 33 is a perspective view of the second connector coupled to a waste collection container of the stool management system.

Now referring primarily to FIGS. 25 through 32, in particular embodiments, the second connector (6) can, but need not necessarily, include a seal element (48) which transitions to a seal open condition (48a) (as shown in the example of FIG. 32) allowing waste matter (15) to flow through the tubular body lumen (2c) within the second connector (6) upon mated engagement of the first and second connectors (5)(6) and toward a seal closed condition (48b) (as shown in the examples of FIGS. 25 through 27) upon disconnecting the first connector (5) from the second connector (6). In particular embodiments, the seal element (48) can be disposed in the tubular body lumen (2c) of the second connector (6) by connecting a seal peripheral edge (48c) to the tubular member internal surface (38a). The seal element (48) can include two or more resiliently flexible wipers (48d) which extend inwardly from the seal peripheral edge (48c) to abut in the seal closed condition (48b). As shown in the illustrative example of FIG. 26, a particular embodiment includes four resiliently flexible wipers (48d) each having a pair of legs (48e)(48f) extending from the center of the seal element (48) defining an angle of about ninety degrees (also referred to as a "cross slit wiper"). Upon insertion of the first tubular portion (36) of the first connector (5) within the tubular member (38) of the second connector (6), each of the resiliently flexible wipers (48) can resiliently bend to travel over the first tubular portion external surface (36c). Upon removal of the first tubular portion (36) of the first connector (5) from the tubular member (38), each of the resiliently flexible wipers (48d) return to abutted engagement of the respective pairs of legs (48e)(48f). A seal element (48) configured in this manner can provide an advantage of forcibly scraping the first tubular portion external surface (36) to remove waste matter (15) as the first tubular portion (36) of the first connector (5) disengages the tubular member (38) of the second connector (6).

Again, referring primarily to FIGS. 23 and 24, embodiments can further include a connector housing (49) disposed about the first tubular portion (36) slidingly telescopingly engaged to the second tubular portion (37). The connector housing (49) can further include a retention tab retaining groove (50) disposed in a connector housing internal surface (49a). As shown in FIG. 24, the retention groove (50) can, but need not necessarily, be an annular retention groove (50a) disposed in the connector housing internal surface (49a); however, this illustrative example is not intended to preclude embodiments in the form of a recess in the internal surface or catch which extends from the internal surface.

Figure 28:
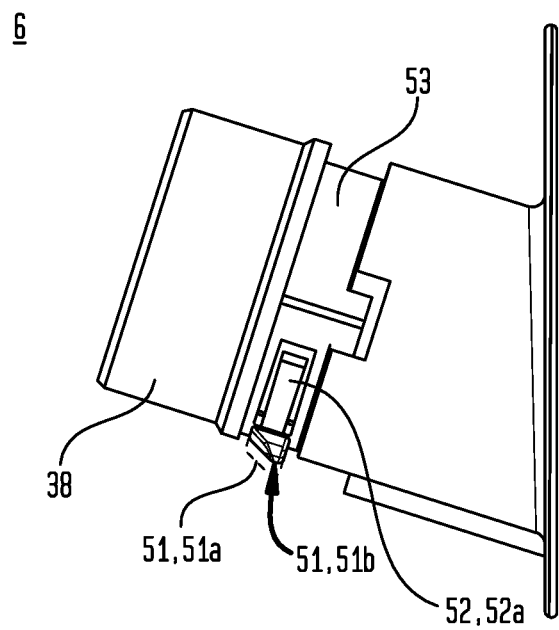
FIG. 28 is a side view of the second connector of the stool management system.
Figure 29:
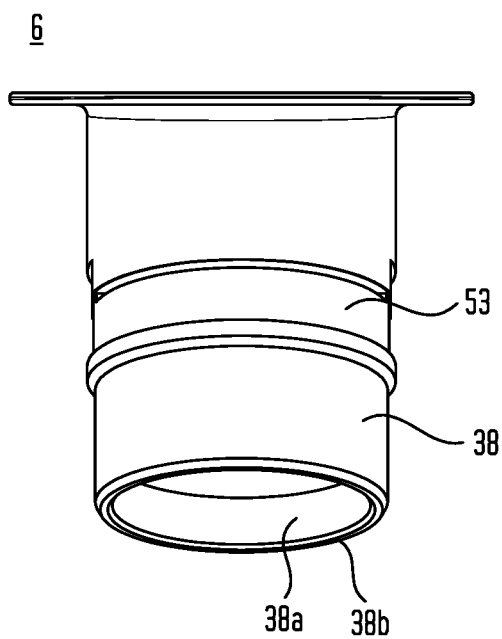
FIG. 29 is a bottom view of the second connector of the stool management system.
Figure 30:
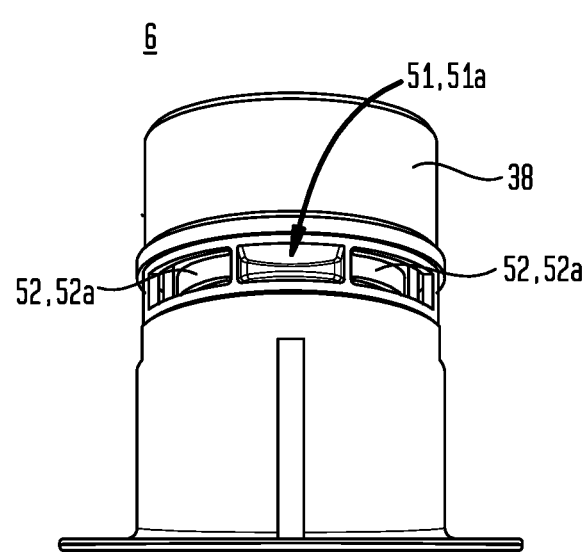
FIG. 30 is a top view of the second connector of the stool management system.
Figure 31:
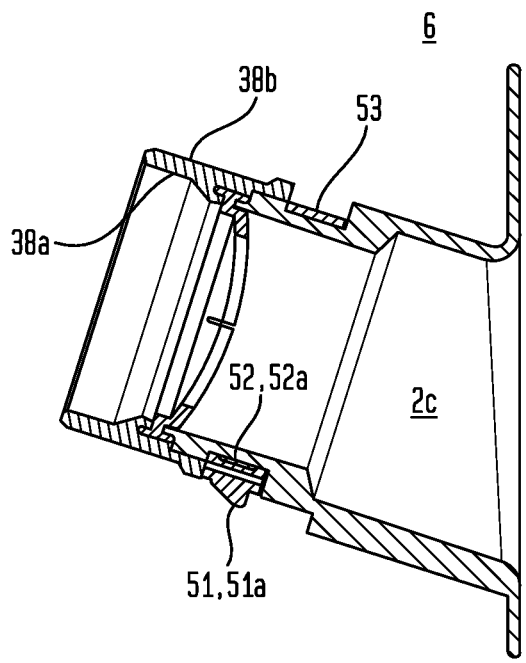
FIG. 31 is cross section view 31-31 of the second connector of the stool management system.

Now referring primarily to FIGS. 26 and 28 through 31, in particular embodiments, the second connector (6) can, but need not necessarily, include a retention tab (51) coupled to the tubular member external surface (38b) of the second connector (6). The retention tab (51) can transition between a retention position (51a) disposed in the retention groove (50) of the connector housing (49) and a release position (51b) disposed outside of the retention groove (50) (as shown in the example of FIG. 28 in broken line). The retention tab (51) can be responsive to a tab bias element (52) which biases movement of the retention tab (51) toward the retention position (51a). In particular embodiments, the tab bias element (51) can comprise one or more resiliently flexible members (52a) coupled or directly connected to the retention tab (51). In the illustrative example, the retention tab (51) and the resiliently flexible member(s) (52a) are included in a one-piece annular band (53) circumferentially disposed about the tubular member external surface (38b). The resiliently flexible member(s) (52a) extend inward to engage and bias the retention tab (51) away from the tubular member external surface (38b) toward the retention position (51a). However, this illustrative example is not intended to preclude embodiments in which the tubular member (38) can be incised between the tubular member internal surface (38a) and the tubular member external surface (38b) to define a tab bias element (52) having a flexible member first end (52b) remaining joined as one piece with the tubular member (38) and a flexible member second end (52c) joined to the retention tab (51). The retention tab (51) being depressible toward the release position (51b).

Figure 20:
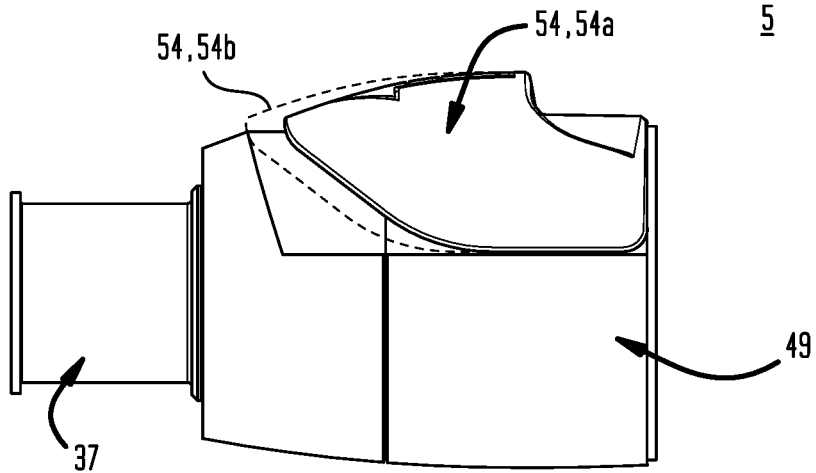
FIG. 20 is a first side view of the first connector of the stool management system.
Figure 21:
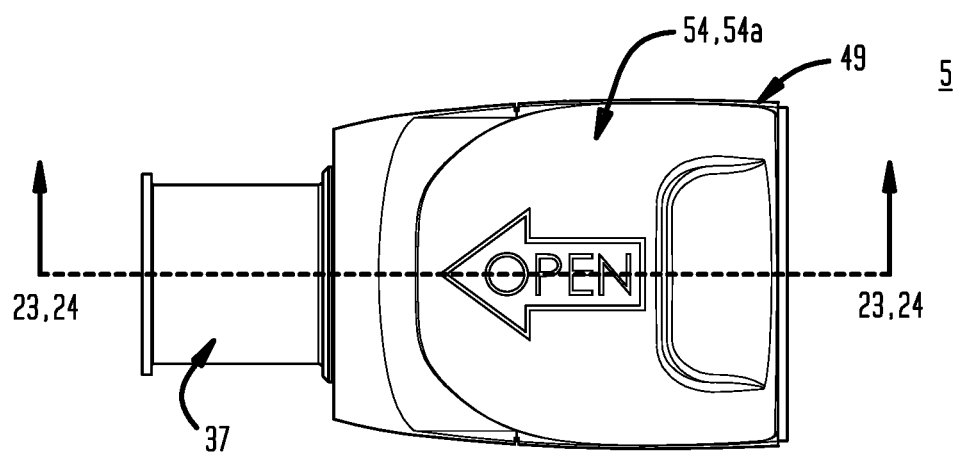
FIG. 21 is a top view of the first connector of the stool management system.
Figure 22:
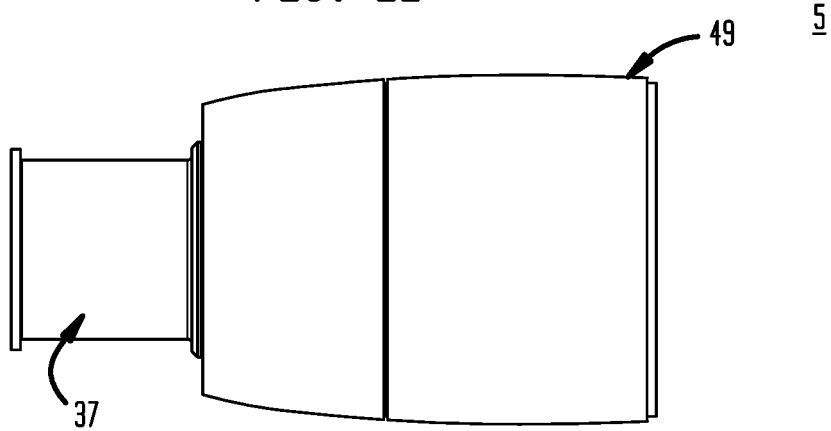
FIG. 22 is a bottom view of the first connector of the stool management system.

Now referring primarily to FIGS. 17 through 24, in particular embodiments, a connector release element (54) slidingly engages the connector housing (49). The connector release element (54) transitions between a secured condition (54a) of the first and second connectors (5)(6) and an unsecured condition (54b) of the first and second connectors (5)(6) (as shown in the example of FIG. 20). As shown in the illustrative example of FIG. 23, the connector release element (54) can include a cammed biasing surface (54c) which moves over the retaining groove (50) with increased biasing as the connector release element (54) moves toward the unsecured condition (54b) of the first and second connectors (5)(6). Now referring to the illustrative example of FIG. 32, the cammed biasing surface (54c) can engage the retention tab (51) to move the retention tab (51) out of said retention groove (50) to the release position (51b) as the connector release element (54) moves toward the unsecured condition (54b).

Now referring primarily to FIG. 32, embodiments include a collection container (7) coupled to or directly connected to the second connector (6).

Now referring primarily to FIGS. 16A and 16B, the tubular body (2) or a portion thereof, can, but need not necessarily, include an antimicrobial agent (57) (shown in the example of FIG. 16B as a stipple). The term "antimicrobial agent" for the purposes of the present invention means an agent which can be combined, overlaid, or applied to a polymeric material in sufficient amounts to kill or inhibit growth of microorganisms in contact with the polymeric material. The term "microorganism" for the purposes of the present invention means any organism of microscopic or submicroscopic size, whether a virus, a single cell organism, or a multicellular organism. Without limitation to the breadth of the foregoing, microorganisms can include viruses; prokaryotes, such as bacteria and archaea; eukaryotes, such as protists, fungi, plants, and animals; or combinations thereof.

In particular embodiments, the tubular body (2) can incorporate the antimicrobial agent (57) as one or more of: polymeric biocides that covalently link bioactive repeating units such as amino, carboxyl, or hydroxyl; biocidal polymers in which the antimicrobial site is embodied by the entire macromolecule; biocide-releasing polymers in which the polymer can be used as a carrier for controlled release of the antimicrobial agent, or biocide entraining polymers in which the polymer entrains but does not substantially release or does not release the antimicrobial agent and efficacy relies on direct contact of microorganisms with the antimicrobial agent entrained in the polymer, and combinations thereof.

Again referring primarily to FIGS. 16A and 16B, in particular embodiments, the tubular body (2) can include the antimicrobial agent (57) in the form of an antimicrobial tubular layer (58) whether as an outer antimicrobial tubular layer (58a) disposed on the tubular body external surface (2b) or as an inner antimicrobial tubular layer (58b) disposed on the tubular body internal surface (2a), or including both the outer antimicrobial tubular layer (58a) and the inner antimicrobial tubular layer (58b) (as shown in the illustrative example of 16B). The antimicrobial layer(s) (58a)(58b) can have a lesser thickness than the tubular body (2). The advantage of providing an antimicrobial layer (58) can be that a lesser amount of antimicrobial agent (57) can be used in providing an antimicrobial layer (58) in comparison to forming the entire tubular body (2) inclusive of the antimicrobial agent (57). As to particular embodiments, such as one-time use or disposable tubular body (2), a lesser cost of production may be desired and achieved by use of an antimicrobial tubular layer (58); however, this example is not intended to preclude embodiments in which the entire or substantially the entirety of the tubular body (2) contains an antimicrobial agent (57).

In particular embodiments, the tubular body (2) or the antimicrobial tubular layers (58a) or (58b) can include an amount of antimicrobial agent (57) in a range of about 0.01% to about 15% by weight, depending upon the antimicrobial agent (57), the application, or combinations thereof. As to particular embodiments, the amount of antimicrobial agent (57) can be selected from the group including or consisting of: about 0.01% to about 1% by weight; about 0.5% to about 1.5% by weight; about 1% to about 2% by weight; about 1.5% to about 2.5% by weight; about 2% to about 3% by weight; about 2.5% to about 3.5% by weight; about 3% to about 4% by weight; about 3.5% to about 4.5% by weight; about 4% to about 5% by weight; about 4.5% to about 5.5% by weight; about 5% to about 6% by weight; about 5.5% to about 6.5% by weight; about 6% to about 7% by weight; about 6.5% to about 7.5% by weight; about 7% to about 8% by weight; about 7.5% to about 8.5% by weight; about 8% to about 9% by weight; about 8.5% to about 9.5% by weight; about 9% to about 10% by weight; about 9.5% to about 10.5% by weight; about 10% to about 11% by weight; about 10.5% to about 11.5% by weight; about 11% to about 12% by weight; about 11.5% to about 12.5% by weight; about 12% to about 13% by weight; about 12.5% to about 13.5% by weight; about 13% to about 14% by weight; about 13.5% to about 14.5% by weight; and about 14% to about 15% by weight, or combinations thereof. However, in particular embodiments, this range may be extended to include a greater percentage by weight with the range similarly incrementally subdivided.

In particular embodiments, the antimicrobial agent (57) can, but need not necessarily, include particles combined with the polymeric material from which the tubular body (2) or antimicrobial layer (58) can be formed, extruded, or co-extruded. The antimicrobial agent (57) can have a median particle size distribution (D50) in a range of about 0.5 micrometers to about 40 micrometers. In other particular embodiments, the antimicrobial agent (57) can have a median particle size distribution (D50) in a range of about 3 micrometers to about 15 micrometers; however, this is not intended to preclude a median particle size distribution (D50) which extends beyond this range such as 1 micrometers to about 40 micrometers; or where the particles obtained have a greater median particle size distribution (D50) and are subsequently reduced by pulverization or sieving to obtain a desired median particle size distribution (D50) based on the application.

In particular embodiments, the antimicrobial agent (57) can be a chlorhexidine, or chlorhexidine salts, and without limitation to the breadth of the foregoing, as examples: 1,1'-hexamethylenebis[5-(4-chlorophenyl)biguanide] hexane powder (CAS Number 55-56-1); chlorohexidine acetate (CAS Number 56-95-1); and chlorhexidine diacetate (CAS Number 4091-99-0), and combinations thereof, which can be combined with the polymeric material for production of the tubular body (2) or the antimicrobial layer (58). The efficacy of the antimicrobial agent (57) such as chlorhexidine whether entrained or released from the polymeric material can, but need not necessarily, be varied as to each portion of the tubular body (2), or varied with respect to the entire tubular body (2) by utilizing different combinations of polymeric material and antimicrobial agent (57) such as, chlorhexidine.

In particular embodiments, the antimicrobial layer(s) (58a)(58b) can be achieved by depositing the antimicrobial agent directly to the tubular body internal surface (2a) or tubular body external surface (2b). As illustrative examples, spray application of chlorhexidine powder directly onto the tubular body internal surface (2a) or tubular body external surface (2b) can be used to establish the antimicrobial layer(s) (58a)58b), or chlorhexidine can be mixed into a polymeric material such as polyurethane, poly(urea)urethane, chitosan, poly (lactide-co-glycolide), or polymethyl methacrylate, and combinations thereof to establish the antimicrobial layer(s) (58a)58b). Again, the efficacy of the entrained chlorhexidine or the release rate of chlorhexidine from the polymeric material can, but need not necessarily, varied as to each portion of the tubular body (2), or varied with respect to the entire tubular body (2) by utilizing different polymeric materials in combination with different forms of chlorhexidine.

As to particular embodiments, the antimicrobial agent (57) can include an amount of elemental silver or silver ions (collectively "silver"). As an illustrative example, elemental silver can take the form of nanoparticles, which may be obtained from Bio-Gate AG, Neumeyerstraße 28-34, 90411 Nürnberg, Germany. As an illustrative example, silver ions can take the form of silver-containing zirconium phosphates, which may be obtained from Milliken & Company, PO Box 1926, Spartanburg, S.C. 29303, United States, or can take the form of silver-containing glasses, which may be obtained from Ciba Specialty Chemicals, Klybeckstrasse 141, CH-4002 Basel, Switzerland, or can take the form of silver-containing zeolites (microporous carriers), which may be obtained from Sciessent, 60 Audubon Road, Wakefield, Mass. 01880, United States.

As to particular embodiments, the antimicrobial agent (57) includes silver-containing zeolites, the amount of silver ions in the zeolites can be in a range of about 0.5% to about 20% by weight of the zeolites. As to other embodiments, the antimicrobial agent (57) includes silver-containing zeolites, the amount of silver ions in the zeolites (such as Product Nos. AJ 10D or LJ 10D, both of which may be obtained from Sciessent, 60 Audubon Road, Wakefield, Mass. 01880, United States) can be around 2.5% by weight of the zeolites.

As to particular embodiments, the antimicrobial layer (58) can include an amount of silver sufficient to kill or inhibit growth of microorganisms. As to particular embodiments, the amount of silver can be in a range of about 0.01% to about 2% by weight of the antimicrobial layer (58).

As to particular embodiments, the antimicrobial agent (57) can include a combination of elements or elemental ions. As an illustrative example, the elements or elemental ions can include silver and zinc. As to particular embodiments, the combination of silver and zinc can include generally similar amounts of silver and zinc.

As to other particular embodiments, the combination of silver and zinc can include a greater amount of silver and a lesser amount of zinc. As to yet other particular embodiments, the combination of zinc and silver can include a lesser amount of silver and a greater amount of zinc.

As to particular embodiments, the combination of silver and zinc can have a ratio in a range of about 1:1 to about 3:1. As an illustrative example, the antimicrobial layer (58) can be formed from polyethylene terephthalate having a combination of silver and zinc in a ratio of about 2:1, whereby the combination of silver and zinc can be in a range of between about 0.5% to about 2% by weight of the tubular body (2) or antimicrobial layer (58).

As to other particular embodiments, the combination of silver and zinc can have a ratio of about 1:1 to about 1:3. As an illustrative example, a tubular body (2) or an inner antimicrobial tubular layer (58*b*) can be formed from polyethylene terephthalate having a combination of silver and zinc in a ratio of about 1:2, whereby the combination of silver and zinc can be in a range of about 0.5% to about 2% by weight of the inner antimicrobial layer (58*b*).

As can be easily understood from the foregoing, the basic concepts of the present invention may be embodied in a variety of ways. The invention involves numerous and varied embodiments of a stool management system (1) and methods for making and using such stool management system (1) including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "seal" should be understood to encompass disclosure of the act of "sealing"—whether explicitly discussed or not—and, conversely, were there effectively disclosure of the act of "sealing", such a disclosure should be understood to encompass disclosure of a "seal" or even a "means for sealing." Such alternative terms for each element or step are to be understood to be explicitly included in the description.

In addition, as to each term used, it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the stool management systems or components herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. An apparatus, comprising:
   a tubular body;
   a first end section disposable in a rectum;
   a second end section including a first connector;
   a collection container including a second connector which mateably engages said first connector:
   wherein said first connector includes:
      a first tubular portion telescopingly engaged to a second tubular portion, said first tubular portion reciprocally telescopingly transitions from an extended condition toward a retracted condition; and
      a vent element disposed in fixed spatial relation to said second tubular portion,
         said vent element transitions between a vent closed condition which engages said first tubular portion in said extended condition and a vent open condition disengaged from said first tubular portion in said retracted condition; and
   wherein said second connector includes:
      a tubular member defining a tubular member internal surface
      a seal element having a seal periphery connected to said tubular member internal surface;
         said seal transitions to a seal open condition, upon said first connector mateably engaged to said second connector.

2. The apparatus of claim 1, further comprising a vent element support which extends from said second tubular portion through a tubular lumen of said first tubular portion to support said vent element in said fixed spatial relation to said first tubular portion.

3. An apparatus, comprising:
   a connector including a first tubular portion reciprocally telescopingly engaged to a second tubular portion, said first tubular portion telescopingly transitions from an extended condition toward a retracted condition;
   a vent element support which extends from said second tubular portion through a tubular lumen of said first tubular portion to support a vent element in fixed spatial relation to said first tubular portion,
   wherein said vent element transitions between a vent closed condition in the extended condition of said first tubular portion and a vent open condition in the retracted condition of said first tubular portion
   wherein said vent element further comprises a porous plug which allows passage of gas from within said first tubular portion.

4. The apparatus of any one of claims 1 and 3, further comprising a first connector housing disposed about said a first tubular portion telescopingly engaged to said second tubular portion.

5. The apparatus of claim 4, further comprising a retention tab retaining groove disposed in an inner surface of said first connector housing.

6. The apparatus of claim 5, further comprising a connector release element slidingly engaged with said first connector housing, said connector release element transitions between a first position in a secured condition of said first and second connectors and a second position in an unsecured condition of said first and second connectors, said connector release element having a cammed biasing surface which moves over said retention tab retaining groove with increased biasing as said connector release moves toward said second position.

7. The apparatus of claim 6, further comprising a retention tab coupled to an external surface of said tubular member of said second connector, said retention tab transitions between a retention position disposable in said retention groove of said first connector housing upon insertion of said first tubular portion of said first connector inside of said tubular member of said second first connector and a release position disposed outside of said retention groove of said first connector.

8. The apparatus of claim 7, further comprising a tab bias element which biases movement of said retention tab toward said retention groove of said first connector housing.

9. The apparatus of claim 6, wherein said cammed biasing surface engages said retention tab to move said retention tab out of said retention groove as said connector release element moves toward said second position.

10. The apparatus of claim 1, wherein said first end section includes a retention cuff disposed about a tubular strut, said retention cuff having retention cuff wall defining an interior space about said tubular strut, said tubular strut increases in diameter approaching said open end of said retention cuff, said retention cuff having a rest volume and an inflated volume.

11. The apparatus of claim 10, wherein said tubular strut tapers proximate said open end of said retention cuff.

12. The apparatus of claim 10, wherein said retention cuff wall having a greater thickness approaching said open end of said retention cuff.

13. The apparatus of claim 10, an inflation lumen disposed within said tubular strut, said inflation lumen defining an inflation passage fluidically coupled to said interior space of said retention cuff.

14. The apparatus of claim 13, further comprising an irrigation lumen disposed within said tubular strut defining an irrigation passage fluidically coupled to said open end of said retention cuff.

15. The apparatus of claim 14, further comprising:
   an inflation port disposed on said external surface of said tubular body, said inflation port connect to said inflation lumen; and
   an irrigation port disposed on an external surface of said tubular body, said irrigation port connected to said irrigation lumen.

16. The apparatus of claim 15, further comprising a sample port which communicates between an internal surface and an external surface of said tubular body.

17. The apparatus of claim 16, further comprising an occlusion balloon.

18. The apparatus of claim 17, wherein said tubular body comprises a union section disposed between an upper tubular body section connected to said retention cuff and a lower section connected to said first connector, said union section including said inflation port and said irrigation port and optionally one or more of said sample port and said substance delivery occlusion balloon.

19. The apparatus of claim 18, wherein said tubular body includes a tubular transsphincteric region disposed between said tubular strut and said upper tubular body.

20. The apparatus of any one of claims 1 and 3, further comprising a bias element which biases movement of said first tubular portion toward said extended condition.

21. The apparatus of claim 3, wherein said vent element comprises an annular peripheral margin disposed about said porous plug.

22. The apparatus of claim 21, further comprising an annular vent seal circumferentially disposed about said annular peripheral margin of said vent element.

23. An apparatus, comprising:
    a first connector including a tubular member defining a tubular member internal surface;
    a seal having a seal peripheral edge connected to said tubular member internal surface,
        said seal element including two or more resiliently flexible wipers inwardly extending from said seal peripheral edge to abut in a seal closed condition
        said tubular member internal surface configured to insertingly receive a tubular portion of a second connector,
        said two or more resiliently flexible wipers flex to engage an external surface of said first tubular portion of said first connector inserted inside of said tubular member,
        whereby said seal element of said second connector transitions to a seal open condition.

24. The apparatus of claim 23, wherein said seal element comprises a cross slit wiper valve having said peripheral margin secured to internal surface of said tubular member and resiliently flexible cross slit wipers which flex to engage said external surface of said tubular portion of said second connector inserted inside of said tubular member.

* * * * *